(12) United States Patent
Tan-Malecki et al.

(10) Patent No.: US 8,623,025 B2
(45) Date of Patent: Jan. 7, 2014

(54) DELIVERY APPARATUS AND METHODS FOR VERTEBROSTENTING

(75) Inventors: Francisca Tan-Malecki, Waltham, MA (US); John V. Hamilton, Foxboro, MA (US); Andrew R. Sennett, Hanover, MA (US); Ronald Sahatjian, Lexington, MA (US); James Coyle, Oranmore (IE); James Cannon, Clarinbridge (IE); Liam Farrissey, Kingston (IE); John Mugan, Moycullen (IE); Martin Bruggemann, Chapelizod (IE); Dion Gallagher, Newmarket on Fergus (IE); Damien Ryan, Galway City (IE)

(73) Assignee: Gmedelaware 2 LLC, Audubon, PA (US)

( * ) Notice: Subject to any disclaimer, the term of this patent is extended or adjusted under 35 U.S.C. 154(b) by 309 days.

(21) Appl. No.: 12/688,437

(22) Filed: Jan. 15, 2010

(65) Prior Publication Data
US 2010/0114111 A1 May 6, 2010

Related U.S. Application Data

(63) Continuation of application No. 11/957,039, filed on Dec. 14, 2007, now Pat. No. 7,909,873.

(60) Provisional application No. 60/875,114, filed on Dec. 15, 2006, provisional application No. 60/875,173, filed on Dec. 15, 2006.

(51) Int. Cl.
*A61B 17/60* (2006.01)
*A61F 2/44* (2006.01)

(52) U.S. Cl.
USPC ............ 606/92; 606/99; 606/105; 623/17.16

(58) Field of Classification Search
USPC ............ 623/1.11–1.12, 17.11–17.16; 606/92–95, 86 R, 90, 99, 105
See application file for complete search history.

(56) References Cited

U.S. PATENT DOCUMENTS

| 3,176,395 A | 4/1965 | Warner et al. |
| 3,875,595 A | 4/1975 | Froning |

(Continued)

FOREIGN PATENT DOCUMENTS

| DE | 10154163 | 5/2003 |
| EP | 1073371 | 2/2001 |

(Continued)

OTHER PUBLICATIONS

Furderer et al. "Vertebral Body Stenting (A method for repositioning and augmenting vertebral body compression fractures)", Der Orthopaedic Apr. 2002, 356-361.

(Continued)

*Primary Examiner* — Ellen C Hammond

(57) ABSTRACT

The invention relates to a systems, devices and methods of delivering and deploying a stent into a curvilinear cavity within a vertebral body or other bony or body structure. In some instances, a system can include an elongate shaft for delivering a self-expanding, cement-directing stent. The elongate shaft can include at least one of an inner shaft, an outer shaft, a tubular sheath, a flexible guidewire, and an internal polymer extrusion. A rotational handle can be used to control movement of the elongate shaft. The rotational handle can incorporate one or more pins in slots associated with each of the components (e.g., inner shaft, outer shaft, and tubular sheath), such that upon rotation of the handle, the pins are forced to move in the direction of their respective slots.

7 Claims, 30 Drawing Sheets

(56) References Cited

U.S. PATENT DOCUMENTS

| | | |
|---|---|---|
| 4,065,817 A | 1/1978 | Branemark et al. |
| 4,313,434 A | 2/1982 | Segal |
| 4,488,549 A | 12/1984 | Lee et al. |
| 4,535,764 A | 8/1985 | Ebert |
| 4,541,423 A | 9/1985 | Barber |
| 4,554,914 A | 11/1985 | Kapp et al. |
| 4,627,434 A | 12/1986 | Murray |
| 4,643,190 A | 2/1987 | Heimberger et al. |
| 4,653,487 A | 3/1987 | Maale |
| 4,653,489 A | 3/1987 | Tronzo |
| 4,693,721 A | 9/1987 | Ducheyne |
| 4,755,184 A | 7/1988 | Silverberg |
| 4,772,264 A | 9/1988 | Cragg |
| 4,820,349 A | 4/1989 | Saab |
| 4,969,888 A | 11/1990 | Scholten et al. |
| 5,002,543 A | 3/1991 | Bradshaw et al. |
| 5,009,661 A | 4/1991 | Michelson |
| 5,015,255 A | 5/1991 | Kuslich |
| 5,030,233 A | 7/1991 | Ducheyne |
| 5,047,055 A | 9/1991 | Bao et al. |
| 5,059,193 A | 10/1991 | Kuslich |
| 5,062,845 A | 11/1991 | Kuslich et al. |
| 5,085,635 A | 2/1992 | Cragg |
| 5,100,423 A | 3/1992 | Fearnot |
| 5,108,404 A | 4/1992 | Scholten et al. |
| 5,192,326 A | 3/1993 | Bao et al. |
| 5,257,994 A | 11/1993 | Lin |
| 5,269,785 A | 12/1993 | Bonutti |
| 5,290,312 A | 3/1994 | Kojimoto et al. |
| 5,322,505 A | 6/1994 | Krause et al. |
| 5,332,402 A | 7/1994 | Teitelbaum |
| 5,342,371 A | 8/1994 | Welter et al. |
| 5,370,653 A | 12/1994 | Cragg |
| 5,397,310 A | 3/1995 | Chu et al. |
| 5,405,377 A | 4/1995 | Cragg |
| 5,437,665 A | 8/1995 | Munro |
| 5,445,639 A | 8/1995 | Kuslich et al. |
| 5,489,274 A | 2/1996 | Chu et al. |
| 5,489,308 A | 2/1996 | Kuslich et al. |
| 5,499,981 A | 3/1996 | Kordis |
| 5,540,693 A | 7/1996 | Fisher |
| 5,549,637 A | 8/1996 | Crainich |
| 5,549,679 A | 8/1996 | Kuslich |
| 5,554,114 A | 9/1996 | Wallace et al. |
| 5,571,189 A | 11/1996 | Kuslich |
| 5,628,788 A | 5/1997 | Pinchuk |
| 5,630,840 A | 5/1997 | Mayer |
| 5,645,545 A | 7/1997 | Bryant |
| 5,645,566 A | 7/1997 | Brenneman et al. |
| 5,665,115 A | 9/1997 | Cragg |
| 5,683,448 A | 11/1997 | Cragg |
| 5,695,513 A | 12/1997 | Johnson et al. |
| 5,716,365 A | 2/1998 | Goicoechea et al. |
| 5,752,969 A | 5/1998 | Cunci et al. |
| 5,759,191 A | 6/1998 | Barbere |
| 5,766,237 A | 6/1998 | Cragg |
| 5,776,180 A | 7/1998 | Goicoechea et al. |
| 5,782,861 A | 7/1998 | Cragg et al. |
| 5,795,331 A | 8/1998 | Cragg et al. |
| 5,807,330 A | 9/1998 | Teitelbaum |
| 5,810,828 A | 9/1998 | Lightman et al. |
| 5,814,044 A | 9/1998 | Hooven |
| 5,827,289 A | 10/1998 | Reiley et al. |
| 5,833,692 A | 11/1998 | Cesarini et al. |
| 5,851,208 A | 12/1998 | Trott |
| 5,868,762 A | 2/1999 | Cragg et al. |
| 5,916,263 A | 6/1999 | Goicoechea et al. |
| 5,928,239 A | 7/1999 | Mirza |
| 5,957,884 A | 9/1999 | Hooven |
| 5,957,974 A | 9/1999 | Thompson et al. |
| 5,972,015 A | 10/1999 | Scribner et al. |
| 5,984,950 A | 11/1999 | Cragg et al. |
| 5,989,223 A | 11/1999 | Chu et al. |
| 5,989,256 A | 11/1999 | Kuslich et al. |
| 6,015,411 A | 1/2000 | Ohkoshi et al. |
| 6,019,786 A | 2/2000 | Thompson |
| 6,051,020 A | 4/2000 | Goicoechea et al. |
| 6,053,922 A | 4/2000 | Krause et al. |
| 6,056,749 A | 5/2000 | Kuslich |
| 6,063,069 A | 5/2000 | Cragg et al. |
| 6,071,300 A | 6/2000 | Brenneman et al. |
| 6,071,301 A | 6/2000 | Cragg et al. |
| 6,086,589 A | 7/2000 | Kuslich et al. |
| 6,086,607 A | 7/2000 | Cragg et al. |
| 6,096,021 A | 8/2000 | Helm et al. |
| 6,096,038 A | 8/2000 | Michelson |
| 6,113,604 A | 9/2000 | Whittaker et al. |
| 6,117,167 A | 9/2000 | Goicoechea et al. |
| 6,127,597 A | 10/2000 | Beyar et al. |
| 6,146,373 A | 11/2000 | Cragg et al. |
| 6,146,422 A | 11/2000 | Lawson |
| 6,149,654 A | 11/2000 | Johnson |
| 6,162,192 A | 12/2000 | Cragg et al. |
| 6,174,328 B1 | 1/2001 | Cragg |
| 6,179,856 B1 | 1/2001 | Barbere |
| 6,199,551 B1 | 3/2001 | Kuslich |
| 6,200,328 B1 | 3/2001 | Cragg et al. |
| 6,203,779 B1 | 3/2001 | Ricci et al. |
| 6,228,120 B1 | 5/2001 | Leonard et al. |
| 6,235,043 B1 | 5/2001 | Reiley et al. |
| 6,241,734 B1 | 6/2001 | Scribner et al. |
| 6,245,107 B1 | 6/2001 | Ferree |
| 6,248,110 B1 | 6/2001 | Reiley et al. |
| 6,248,131 B1 | 6/2001 | Felt et al. |
| 6,258,089 B1 | 7/2001 | Campbell et al. |
| 6,261,293 B1 | 7/2001 | Nicholson et al. |
| 6,280,456 B1 | 8/2001 | Scribner et al. |
| 6,302,906 B1 | 10/2001 | Goicoechea et al. |
| 6,303,100 B1 | 10/2001 | Ricci et al. |
| 6,306,177 B1 | 10/2001 | Felt et al. |
| 6,309,396 B1 | 10/2001 | Ritland |
| 6,315,753 B1 | 11/2001 | Cragg et al. |
| 6,315,789 B1 | 11/2001 | Cragg |
| 6,319,255 B1 | 11/2001 | Grundei et al. |
| RE37,479 E | 12/2001 | Kuslich |
| 6,337,142 B2 | 1/2002 | Harder et al. |
| 6,342,068 B1 | 1/2002 | Thompson |
| 6,346,117 B1 | 2/2002 | Greenhalgh |
| 6,348,066 B1 | 2/2002 | Pinchuk et al. |
| 6,364,895 B1 | 4/2002 | Greenhalgh |
| 6,371,974 B1 | 4/2002 | Brenneman et al. |
| 6,375,670 B1 | 4/2002 | Greenhalgh |
| 6,383,188 B2 | 5/2002 | Kuslich et al. |
| 6,387,122 B1 | 5/2002 | Cragg |
| 6,391,037 B1 | 5/2002 | Greenhalgh |
| 6,395,032 B1 | 5/2002 | Gauchet et al. |
| 6,395,034 B1 | 5/2002 | Suddaby |
| 6,402,784 B1 | 6/2002 | Wardlaw et al. |
| 6,423,083 B2 | 7/2002 | Reiley et al. |
| 6,440,138 B1 | 8/2002 | Reiley et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,458,127 B1 | 10/2002 | Truckai et al. |
| 6,475,466 B1 | 11/2002 | Ricci et al. |
| 6,488,710 B2 | 12/2002 | Besselink et al. |
| 6,508,839 B1 | 1/2003 | Lambrecht et al. |
| 6,511,468 B1 | 1/2003 | Cragg et al. |
| 6,514,258 B1 | 2/2003 | Brown et al. |
| 6,527,734 B2 | 3/2003 | Cragg et al. |
| 6,533,751 B2 | 3/2003 | Cragg et al. |
| 6,533,817 B1 | 3/2003 | Norton et al. |
| 6,540,739 B2 | 4/2003 | Lechot et al. |
| 6,544,236 B1 | 4/2003 | Cragg et al. |
| 6,558,367 B1 | 5/2003 | Cragg et al. |
| 6,558,386 B1 | 5/2003 | Cragg |
| 6,558,390 B2 | 5/2003 | Cragg |
| 6,575,978 B2 | 6/2003 | Peterson et al. |
| 6,575,979 B1 | 6/2003 | Cragg |
| 6,582,467 B1 | 6/2003 | Teitelbaum et al. |
| 6,592,617 B2 | 7/2003 | Thompson |
| 6,607,544 B1 | 8/2003 | Boucher et al. |
| 6,610,026 B2 | 8/2003 | Cragg et al. |
| 6,620,162 B2 | 9/2003 | Kuslich et al. |

(56) References Cited

U.S. PATENT DOCUMENTS

| | | |
|---|---|---|
| 6,620,169 B1 | 9/2003 | Peterson et al. |
| 6,626,907 B2 | 9/2003 | Campbell et al. |
| 6,632,235 B2 | 10/2003 | Weikel et al. |
| 6,635,027 B1 | 10/2003 | Cragg et al. |
| 6,641,587 B2 | 11/2003 | Scribner et al. |
| 6,641,607 B1 | 11/2003 | Hossainy et al. |
| 6,656,185 B2 | 12/2003 | Gleason et al. |
| 6,663,647 B2 | 12/2003 | Reiley et al. |
| 6,673,101 B1 | 1/2004 | Fitzgerald et al. |
| 6,679,886 B2 | 1/2004 | Weikel et al. |
| 6,689,162 B1 | 2/2004 | Thompson |
| 6,692,459 B2 | 2/2004 | Teitelbaum |
| 6,706,044 B2 | 3/2004 | Kuslich et al. |
| 6,709,435 B2 | 3/2004 | Lin |
| 6,712,819 B2 | 3/2004 | Zucherman et al. |
| 6,712,853 B2 | 3/2004 | Kuslich |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,740,090 B1 | 5/2004 | Cragg et al. |
| 6,740,093 B2 | 5/2004 | Hochschuler et al. |
| 6,749,614 B2 | 6/2004 | Teitelbaum et al. |
| 6,780,189 B2 | 8/2004 | Tidwell et al. |
| 6,786,903 B2 | 9/2004 | Lin |
| 6,790,210 B1 | 9/2004 | Cragg et al. |
| 6,796,988 B2 | 9/2004 | Melkent et al. |
| 6,805,697 B1 | 10/2004 | Helm et al. |
| 6,814,754 B2 | 11/2004 | Greenhalgh |
| 6,821,277 B2 | 11/2004 | Teitelbaum |
| 6,824,087 B2 | 11/2004 | McPherson et al. |
| 6,827,743 B2 | 12/2004 | Eisermann et al. |
| 6,849,086 B2 | 2/2005 | Cragg |
| 6,863,672 B2 | 3/2005 | Reiley et al. |
| 6,869,445 B1 | 3/2005 | Johnson |
| 6,875,212 B2 | 4/2005 | Shaolian et al. |
| 6,875,219 B2 | 4/2005 | Arramon et al. |
| 6,896,677 B1 | 5/2005 | Lin et al. |
| 6,899,713 B2 | 5/2005 | Shaolian et al. |
| 6,899,716 B2 | 5/2005 | Cragg |
| 6,899,719 B2 | 5/2005 | Reiley et al. |
| 6,921,403 B2 | 7/2005 | Cragg et al. |
| 6,923,811 B1 | 8/2005 | Carl et al. |
| 6,923,813 B2 | 8/2005 | Phillips et al. |
| 6,929,659 B2 | 8/2005 | Pinchuk |
| 6,951,562 B2 | 10/2005 | Zwirnmann |
| 6,958,061 B2 | 10/2005 | Truckai et al. |
| 6,960,215 B2 | 11/2005 | Olson, Jr. et al. |
| 6,964,657 B2 | 11/2005 | Cragg et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 6,984,219 B2 | 1/2006 | Ashby et al. |
| 6,997,929 B2 | 2/2006 | Manzi et al. |
| 7,008,424 B2 | 3/2006 | Teitelbaum |
| 7,011,661 B2 | 3/2006 | Riedel et al. |
| 7,014,633 B2 | 3/2006 | Cragg |
| 7,025,771 B2 | 4/2006 | Kuslich et al. |
| 7,037,323 B2 | 5/2006 | Sing et al. |
| 7,044,954 B2 | 5/2006 | Reiley et al. |
| 7,048,710 B1 | 5/2006 | Cragg et al. |
| 7,056,317 B2 | 6/2006 | Lechot et al. |
| 7,056,345 B2 | 6/2006 | Kuslich |
| 7,063,703 B2 | 6/2006 | Reo |
| 7,081,122 B1 | 7/2006 | Reiley et al. |
| 7,083,621 B2 | 8/2006 | Shaolian et al. |
| 7,087,055 B2 | 8/2006 | Lim et al. |
| 7,087,058 B2 | 8/2006 | Cragg |
| 7,114,501 B2 | 10/2006 | Johnson et al. |
| 7,122,043 B2 | 10/2006 | Greenhalgh et al. |
| 7,122,052 B2 | 10/2006 | Greenhalgh |
| 7,131,605 B2 | 11/2006 | McPherson et al. |
| 7,135,021 B2 | 11/2006 | Lin et al. |
| 7,141,074 B2 | 11/2006 | Fanger et al. |
| 7,147,650 B2 | 12/2006 | Lee |
| 7,153,306 B2 | 12/2006 | Ralph et al. |
| 7,153,307 B2 | 12/2006 | Scribner et al. |
| 7,175,627 B2 | 2/2007 | Lin et al. |
| 7,175,628 B2 | 2/2007 | Lin et al. |
| 7,175,629 B2 | 2/2007 | Lin et al. |
| 7,175,646 B2 | 2/2007 | Brenneman et al. |
| 7,179,024 B2 | 2/2007 | Greenhalgh |
| 7,192,436 B2 | 3/2007 | Sing et al. |
| 7,201,725 B1 | 4/2007 | Cragg et al. |
| 7,220,282 B2 | 5/2007 | Kuslich |
| 7,226,481 B2 | 6/2007 | Kuslich |
| 7,234,468 B2 | 6/2007 | Johnson et al. |
| 7,241,297 B2 | 7/2007 | Shaolian et al. |
| 7,309,338 B2 | 12/2007 | Cragg |
| 7,311,713 B2 | 12/2007 | Johnson et al. |
| 7,312,826 B2 | 12/2007 | Ishii |
| RE39,995 E | 1/2008 | Pepper et al. |
| 7,318,826 B2 | 1/2008 | Teitelbaum et al. |
| 7,329,259 B2 | 2/2008 | Cragg |
| 7,329,268 B2 | 2/2008 | Van Nguyen et al. |
| 7,338,513 B2 | 3/2008 | Lee et al. |
| 7,364,582 B2 | 4/2008 | Lee |
| D583,051 S | 12/2008 | Lee et al. |
| 7,465,318 B2 | 12/2008 | Sennett et al. |
| 2001/0034509 A1 | 10/2001 | Cragg et al. |
| 2001/0034526 A1 | 10/2001 | Kuslich et al. |
| 2001/0041913 A1 | 11/2001 | Cragg et al. |
| 2001/0044647 A1 | 11/2001 | Pinchuk et al. |
| 2001/0049527 A1 | 12/2001 | Cragg |
| 2001/0049554 A1 | 12/2001 | Ruiz et al. |
| 2001/0056254 A1 | 12/2001 | Cragg et al. |
| 2001/0056299 A1 | 12/2001 | Thompson |
| 2002/0010442 A1 | 1/2002 | Teitelbaum |
| 2002/0010472 A1 | 1/2002 | Kuslich et al. |
| 2002/0013616 A1 | 1/2002 | Carter et al. |
| 2002/0016583 A1 | 2/2002 | Cragg |
| 2002/0016611 A1 | 2/2002 | Cragg et al. |
| 2002/0019659 A1 | 2/2002 | Goicoechea et al. |
| 2002/0022822 A1 | 2/2002 | Cragg et al. |
| 2002/0022856 A1 | 2/2002 | Johnson et al. |
| 2002/0034493 A1 | 3/2002 | Ricci et al. |
| 2002/0058947 A1 | 5/2002 | Hochschuler et al. |
| 2002/0058992 A1 | 5/2002 | Greenhalgh |
| 2002/0062104 A1 | 5/2002 | Ashby et al. |
| 2002/0062106 A1 | 5/2002 | Chu et al. |
| 2002/0066360 A1 | 6/2002 | Greenhalgh et al. |
| 2002/0068974 A1 | 6/2002 | Kuslich et al. |
| 2002/0068975 A1 | 6/2002 | Teitelbaum et al. |
| 2002/0077701 A1 | 6/2002 | Kuslich |
| 2002/0082598 A1 | 6/2002 | Teitelbaum |
| 2002/0082600 A1 | 6/2002 | Shaolian et al. |
| 2002/0091372 A1 | 7/2002 | Cragg et al. |
| 2002/0116013 A1 | 8/2002 | Gleason et al. |
| 2002/0116051 A1 | 8/2002 | Cragg |
| 2002/0123750 A1 | 9/2002 | Eisermann et al. |
| 2002/0156495 A1 | 10/2002 | Brenneman et al. |
| 2002/0169449 A1 | 11/2002 | Kuslich et al. |
| 2002/0173796 A1 | 11/2002 | Cragg |
| 2002/0173813 A1 | 11/2002 | Peterson et al. |
| 2002/0183761 A1 | 12/2002 | Johnson et al. |
| 2002/0188300 A1 | 12/2002 | Arramon et al. |
| 2002/0198526 A1 | 12/2002 | Shaolian et al. |
| 2003/0018292 A1 | 1/2003 | Kuslich et al. |
| 2003/0040733 A1 | 2/2003 | Cragg et al. |
| 2003/0068296 A1 | 4/2003 | Ricci et al. |
| 2003/0074075 A1 | 4/2003 | Thomas et al. |
| 2003/0082169 A1 | 5/2003 | Boyd |
| 2003/0083642 A1 | 5/2003 | Boyd et al. |
| 2003/0083669 A1 | 5/2003 | Gleason |
| 2003/0083746 A1 | 5/2003 | Kuslich |
| 2003/0083749 A1 | 5/2003 | Kuslich et al. |
| 2003/0088249 A1 | 5/2003 | Furderer |
| 2003/0088271 A1 | 5/2003 | Cragg et al. |
| 2003/0105469 A1 | 6/2003 | Karmon |
| 2003/0108589 A1 | 6/2003 | Lacout et al. |
| 2003/0135237 A1 | 7/2003 | Cragg et al. |
| 2003/0149472 A1 | 8/2003 | Pinchuk et al. |
| 2003/0153971 A1 | 8/2003 | Chandrasekaran |
| 2003/0158557 A1 | 8/2003 | Cragg et al. |
| 2003/0181982 A1 | 9/2003 | Kuslich |

(56) References Cited

U.S. PATENT DOCUMENTS

| | | |
|---|---|---|
| 2003/0187433 A1 | 10/2003 | Lin |
| 2003/0191474 A1 | 10/2003 | Cragg et al. |
| 2003/0195518 A1 | 10/2003 | Cragg |
| 2003/0195611 A1 | 10/2003 | Greenhalgh et al. |
| 2003/0204189 A1 | 10/2003 | Cragg |
| 2003/0208263 A1 | 11/2003 | Burmeister et al. |
| 2003/0211135 A1 | 11/2003 | Greenhalgh et al. |
| 2003/0220649 A1 | 11/2003 | Bao et al. |
| 2003/0225391 A1 | 12/2003 | Cragg et al. |
| 2003/0229353 A1 | 12/2003 | Cragg |
| 2003/0233096 A1 | 12/2003 | Osorio et al. |
| 2004/0006341 A1 | 1/2004 | Shaolian et al. |
| 2004/0006344 A1 | 1/2004 | Nguyen et al. |
| 2004/0019354 A1 | 1/2004 | Johnson et al. |
| 2004/0033364 A1 | 2/2004 | Spiridigliozzi et al. |
| 2004/0051201 A1 | 3/2004 | Greenhalgh et al. |
| 2004/0064144 A1 | 4/2004 | Johnson et al. |
| 2004/0073139 A1 | 4/2004 | Hirsch et al. |
| 2004/0073287 A1 | 4/2004 | Goicoechea et al. |
| 2004/0073293 A1 | 4/2004 | Thompson |
| 2004/0073308 A1 | 4/2004 | Kuslich et al. |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0092993 A1 | 5/2004 | Teitelbaum et al. |
| 2004/0098086 A1 | 5/2004 | Goicoechea et al. |
| 2004/0098115 A1 | 5/2004 | Goicoechea et al. |
| 2004/0102774 A1 | 5/2004 | Trieu |
| 2004/0106940 A1 | 6/2004 | Shaolian et al. |
| 2004/0106979 A1 | 6/2004 | Goicoechea et al. |
| 2004/0106999 A1 | 6/2004 | Mathews |
| 2004/0133220 A1 | 7/2004 | Lashinski et al. |
| 2004/0138707 A1 | 7/2004 | Greenhalgh |
| 2004/0138744 A1 | 7/2004 | Lashinski et al. |
| 2004/0147934 A1 | 7/2004 | Kiester |
| 2004/0153146 A1 | 8/2004 | Lashinski et al. |
| 2004/0158287 A1 | 8/2004 | Cragg et al. |
| 2004/0162559 A1 | 8/2004 | Arramon et al. |
| 2004/0167562 A1 | 8/2004 | Osorio et al. |
| 2004/0167599 A1 | 8/2004 | Goicoechea et al. |
| 2004/0176723 A1 | 9/2004 | Sing et al. |
| 2004/0181191 A1 | 9/2004 | Teitelbaum |
| 2004/0186480 A1 | 9/2004 | Lin et al. |
| 2004/0186481 A1 | 9/2004 | Chern Lin et al. |
| 2004/0186576 A1 | 9/2004 | Biscup et al. |
| 2004/0208717 A1 | 10/2004 | Greenhalgh |
| 2004/0210297 A1 | 10/2004 | Lin et al. |
| 2004/0215190 A1 | 10/2004 | Nguyen et al. |
| 2004/0215193 A1 | 10/2004 | Shaolian et al. |
| 2004/0215343 A1 | 10/2004 | Hochschuler et al. |
| 2004/0215344 A1 | 10/2004 | Hochschuler et al. |
| 2004/0220577 A1 | 11/2004 | Cragg et al. |
| 2004/0220580 A1 | 11/2004 | Johnson et al. |
| 2004/0220593 A1 | 11/2004 | Greenhalgh |
| 2004/0220615 A1 | 11/2004 | Lin et al. |
| 2004/0220672 A1 | 11/2004 | Shadduck |
| 2004/0225296 A1 | 11/2004 | Reiss et al. |
| 2004/0230198 A1 | 11/2004 | Manzi et al. |
| 2004/0249382 A1 | 12/2004 | Olson et al. |
| 2005/0010297 A1 | 1/2005 | Watson et al. |
| 2005/0013194 A1 | 1/2005 | Vaage et al. |
| 2005/0026178 A1 | 2/2005 | Nilsen-Hamilton |
| 2005/0033292 A1 | 2/2005 | Teitelbaum et al. |
| 2005/0033360 A1 | 2/2005 | Sing et al. |
| 2005/0038432 A1 | 2/2005 | Shaolian et al. |
| 2005/0038514 A1 | 2/2005 | Helm et al. |
| 2005/0043733 A1 | 2/2005 | Eisermann et al. |
| 2005/0043737 A1 | 2/2005 | Reiley et al. |
| 2005/0049681 A1 | 3/2005 | Greenhalgh et al. |
| 2005/0055047 A1 | 3/2005 | Greenhalgh |
| 2005/0055094 A1 | 3/2005 | Kuslich |
| 2005/0070908 A1 | 3/2005 | Cragg |
| 2005/0080476 A1* | 4/2005 | Gunderson et al. ......... 623/1.11 |
| 2005/0085903 A1 | 4/2005 | Lau |
| 2005/0090852 A1 | 4/2005 | Layne et al. |
| 2005/0113843 A1 | 5/2005 | Arramon |
| 2005/0113919 A1 | 5/2005 | Cragg et al. |
| 2005/0113928 A1 | 5/2005 | Cragg et al. |
| 2005/0113929 A1 | 5/2005 | Cragg et al. |
| 2005/0124999 A1 | 6/2005 | Teitelbaum et al. |
| 2005/0130929 A1 | 6/2005 | Boyd |
| 2005/0131417 A1 | 6/2005 | Ahern et al. |
| 2005/0131516 A1 | 6/2005 | Greenhalgh |
| 2005/0131529 A1 | 6/2005 | Cragg |
| 2005/0137601 A1 | 6/2005 | Assell et al. |
| 2005/0137602 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0137612 A1 | 6/2005 | Assell et al. |
| 2005/0143737 A1 | 6/2005 | Pafford et al. |
| 2005/0143823 A1 | 6/2005 | Boyd et al. |
| 2005/0143827 A1 | 6/2005 | Globerman et al. |
| 2005/0149022 A1 | 7/2005 | Shaolian et al. |
| 2005/0149034 A1 | 7/2005 | Assell et al. |
| 2005/0149049 A1 | 7/2005 | Assell et al. |
| 2005/0149191 A1 | 7/2005 | Cragg et al. |
| 2005/0165406 A1 | 7/2005 | Assell et al. |
| 2005/0170120 A1 | 8/2005 | Teitelbaum et al. |
| 2005/0171552 A1 | 8/2005 | Johnson et al. |
| 2005/0182414 A1 | 8/2005 | Manzi et al. |
| 2005/0182417 A1 | 8/2005 | Pagano |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0187605 A1 | 8/2005 | Greenhalgh et al. |
| 2005/0209555 A1 | 9/2005 | Middleton et al. |
| 2005/0209595 A1 | 9/2005 | Karmon |
| 2005/0216018 A1 | 9/2005 | Sennett |
| 2005/0222605 A1 | 10/2005 | Greenhalgh et al. |
| 2005/0228417 A1 | 10/2005 | Teitelbaum et al. |
| 2005/0234453 A1 | 10/2005 | Shaolian et al. |
| 2005/0251140 A1 | 11/2005 | Shaolian et al. |
| 2005/0261684 A1 | 11/2005 | Shaolian et al. |
| 2005/0261689 A1 | 11/2005 | Lin |
| 2005/0261695 A1 | 11/2005 | Cragg et al. |
| 2005/0261781 A1 | 11/2005 | Sennett et al. |
| 2005/0267483 A1 | 12/2005 | Middleton |
| 2005/0277946 A1 | 12/2005 | Greenhalgh |
| 2005/0277978 A1 | 12/2005 | Greenhalgh |
| 2005/0278036 A1 | 12/2005 | Leonard et al. |
| 2005/0283040 A1 | 12/2005 | Greenhalgh |
| 2005/0283166 A1 | 12/2005 | Greenhalgh |
| 2006/0004326 A1 | 1/2006 | Collins et al. |
| 2006/0004455 A1 | 1/2006 | Leonard et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009799 A1 | 1/2006 | Kleshinski et al. |
| 2006/0009851 A1 | 1/2006 | Collins et al. |
| 2006/0020287 A1 | 1/2006 | Lee et al. |
| 2006/0028986 A1 | 2/2006 | Kwon et al. |
| 2006/0036276 A1 | 2/2006 | Nguyen et al. |
| 2006/0052800 A1 | 3/2006 | Greenhalgh |
| 2006/0058800 A1 | 3/2006 | Ainsworth et al. |
| 2006/0058807 A1 | 3/2006 | Landry et al. |
| 2006/0058880 A1 | 3/2006 | Wysocki et al. |
| 2006/0064101 A1 | 3/2006 | Arramon |
| 2006/0089715 A1 | 4/2006 | Truckai et al. |
| 2006/0095074 A1 | 5/2006 | Lee et al. |
| 2006/0095138 A1 | 5/2006 | Truckai et al. |
| 2006/0100706 A1 | 5/2006 | Shadduck et al. |
| 2006/0106305 A1 | 5/2006 | Lau |
| 2006/0106403 A1 | 5/2006 | Schaller |
| 2006/0106459 A1 | 5/2006 | Truckai et al. |
| 2006/0116690 A1 | 6/2006 | Pagano |
| 2006/0116757 A1 | 6/2006 | Lashinski et al. |
| 2006/0122622 A1 | 6/2006 | Truckai et al. |
| 2006/0122623 A1 | 6/2006 | Truckai et al. |
| 2006/0133193 A1 | 6/2006 | Arramon |
| 2006/0142779 A1 | 6/2006 | Arramon et al. |

(56) References Cited

U.S. PATENT DOCUMENTS

| | | |
|---|---|---|
| 2006/0142795 A1 | 6/2006 | Nguyen et al. |
| 2006/0149268 A1 | 7/2006 | Truckai et al. |
| 2006/0149379 A1 | 7/2006 | Kuslich et al. |
| 2006/0161166 A1 | 7/2006 | Johnson et al. |
| 2006/0164913 A1 | 7/2006 | Arramon |
| 2006/0178694 A1 | 8/2006 | Greenhalgh et al. |
| 2006/0178743 A1 | 8/2006 | Carter |
| 2006/0184188 A1 | 8/2006 | Li et al. |
| 2006/0184192 A1 | 8/2006 | Markworth et al. |
| 2006/0206209 A1 | 9/2006 | Cragg et al. |
| 2006/0229625 A1 | 10/2006 | Truckai et al. |
| 2006/0229628 A1 | 10/2006 | Truckai et al. |
| 2006/0229629 A1 | 10/2006 | Manzi et al. |
| 2006/0230986 A1 | 10/2006 | Hoffis |
| 2006/0235425 A1 | 10/2006 | Lin et al. |
| 2006/0241644 A1 | 10/2006 | Osorio et al. |
| 2006/0241671 A1 | 10/2006 | Greenhalgh |
| 2006/0264957 A1 | 11/2006 | Cragg et al. |
| 2006/0264965 A1 | 11/2006 | Shadduck et al. |
| 2006/0293663 A1 | 12/2006 | Walkenhorst et al. |
| 2006/0293748 A1 | 12/2006 | Alexander et al. |
| 2007/0010717 A1 | 1/2007 | Cragg |
| 2007/0010844 A1 | 1/2007 | Gong et al. |
| 2007/0010845 A1 | 1/2007 | Gong et al. |
| 2007/0016194 A1 | 1/2007 | Shaolian et al. |
| 2007/0016283 A1 | 1/2007 | Greenhalgh et al. |
| 2007/0021737 A1 | 1/2007 | Lee |
| 2007/0032791 A1 | 2/2007 | Greenhalgh |
| 2007/0055260 A1 | 3/2007 | Cragg |
| 2007/0055261 A1 | 3/2007 | Reiley et al. |
| 2007/0055266 A1 | 3/2007 | Osorio et al. |
| 2007/0055275 A1 | 3/2007 | Schaller |
| 2007/0055285 A1 | 3/2007 | Osorio et al. |
| 2007/0066977 A1 | 3/2007 | Assell et al. |
| 2007/0067034 A1 | 3/2007 | Chirico et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0100452 A1 | 5/2007 | Prosser |
| 2007/0112427 A1 | 5/2007 | Christy et al. |
| 2007/0123877 A1 | 5/2007 | Goldin et al. |
| 2007/0123936 A1 | 5/2007 | Goldin et al. |
| 2007/0129669 A1 | 6/2007 | Lin et al. |
| 2007/0129670 A1 | 6/2007 | Lin et al. |
| 2007/0142765 A1 | 6/2007 | Lin et al. |
| 2007/0149994 A1 | 6/2007 | Sosnowski et al. |
| 2007/0185231 A1 | 8/2007 | Liu et al. |
| 2007/0197861 A1 | 8/2007 | Reiley et al. |
| 2007/0198020 A1 | 8/2007 | Reiley et al. |
| 2007/0213827 A1 | 9/2007 | Arramon |
| 2007/0219634 A1 | 9/2007 | Greenhalgh et al. |
| 2007/0233099 A1 | 10/2007 | Cragg |
| 2007/0233260 A1 | 10/2007 | Cragg |
| 2007/0244358 A1 | 10/2007 | Lee |
| 2007/0260270 A1 | 11/2007 | Assell et al. |
| 2007/0265697 A1 | 11/2007 | Goicoechea et al. |
| 2007/0276430 A1 | 11/2007 | Lee et al. |
| 2007/0282371 A1 | 12/2007 | Lee et al. |
| 2007/0282373 A1 | 12/2007 | Ashby et al. |
| 2008/0004707 A1 | 1/2008 | Cragg et al. |
| 2008/0015631 A1 | 1/2008 | Lee et al. |
| 2008/0015639 A1 | 1/2008 | Bjork et al. |
| 2008/0027456 A1 | 1/2008 | Truckai et al. |
| 2008/0027542 A1 | 1/2008 | McQuillan et al. |
| 2008/0045881 A1 | 2/2008 | Teitelbaum et al. |
| 2008/0045922 A1 | 2/2008 | Cragg et al. |
| 2008/0046000 A1 | 2/2008 | Lee et al. |
| 2008/0065076 A1 | 3/2008 | Cragg et al. |
| 2008/0065080 A1 | 3/2008 | Assell et al. |
| 2008/0065083 A1 | 3/2008 | Truckai et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0065116 A1 | 3/2008 | Lee et al. |
| 2008/0065190 A1 | 3/2008 | Osorio et al. |
| 2008/0071278 A1 | 3/2008 | Assell et al. |
| 2008/0071281 A1 | 3/2008 | Wilson et al. |
| 2008/0071282 A1 | 3/2008 | Assell et al. |
| 2008/0071283 A1 | 3/2008 | Osorio et al. |
| 2008/0071356 A1 | 3/2008 | Greenhalgh et al. |
| 2008/0086133 A1 | 4/2008 | Kuslich et al. |
| 2008/0097332 A1 | 4/2008 | Greenhalgh et al. |
| 2008/0097511 A1 | 4/2008 | Yuan et al. |
| 2008/0113008 A1 | 5/2008 | Roche |
| 2008/0114364 A1 | 5/2008 | Goldin et al. |
| 2008/0119858 A1 | 5/2008 | Potash |
| 2008/0119886 A1 | 5/2008 | Greenhalgh et al. |
| 2008/0132899 A1 | 6/2008 | Shadduck et al. |
| 2008/0154304 A1 | 6/2008 | Crawford et al. |
| 2008/0161825 A1 | 7/2008 | Greenhalgh et al. |
| 2008/0161854 A1 | 7/2008 | Bae et al. |
| 2008/0167657 A1 | 7/2008 | Greenhalgh |
| 2008/0172060 A1 | 7/2008 | Collins et al. |
| 2008/0183105 A1 | 7/2008 | Greenhalgh et al. |
| 2008/0183204 A1 | 7/2008 | Greenhalgh et al. |
| 2008/0195112 A1 | 8/2008 | Liu et al. |
| 2008/0200915 A1 | 8/2008 | Globerman et al. |
| 2008/0255420 A1 | 10/2008 | Lee et al. |
| 2008/0262492 A1 | 10/2008 | Lee |
| 2008/0262537 A1 | 10/2008 | Lee et al. |
| 2008/0269727 A1 | 10/2008 | Lee |
| 2008/0269761 A1 | 10/2008 | Truckai et al. |
| 2008/0269766 A1 | 10/2008 | Justis |
| 2008/0281346 A1 | 11/2008 | Greenhalgh et al. |
| 2008/0281364 A1 | 11/2008 | Chirico et al. |
| 2008/0294191 A1 | 11/2008 | Lee |
| 2008/0294204 A1 | 11/2008 | Chirico et al. |
| 2009/0005782 A1 | 1/2009 | Chirico et al. |
| 2009/0005821 A1 | 1/2009 | Chirico et al. |
| 2009/0012564 A1 | 1/2009 | Chirico et al. |
| 2009/0023995 A1 | 1/2009 | Lee |
| 2009/0069842 A1 | 3/2009 | Lee et al. |
| 2009/0171147 A1 | 7/2009 | Lee et al. |
| 2009/0216260 A1 | 8/2009 | Souza et al. |
| 2009/0234398 A1 | 9/2009 | Chirico et al. |
| 2011/0093007 A1* | 4/2011 | Abbott et al. ............... 606/213 |
| 2011/0196499 A1* | 8/2011 | Boucher et al. ............ 623/17.16 |

FOREIGN PATENT DOCUMENTS

| | | |
|---|---|---|
| EP | 1308134 | 5/2003 |
| EP | 1463464 | 10/2004 |
| EP | 1498079 | 1/2005 |
| ES | 2280474 | 9/2007 |
| JP | 2003180700 | 7/2003 |
| NL | 9001858 A | 3/1992 |
| NL | 1009471 | 12/1999 |
| WO | WO-9304634 A1 | 3/1993 |
| WO | WO-9826725 A1 | 6/1998 |
| WO | WO-9962416 A1 | 12/1999 |
| WO | WO-0100408 A1 | 1/2001 |
| WO | WO-0160270 A1 | 8/2001 |
| WO | WO-0226170 A2 | 4/2002 |
| WO | WO-03000951 A1 | 1/2003 |
| WO | WO-03057088 A1 | 7/2003 |
| WO | WO-03101308 A1 | 12/2003 |
| WO | WO-2004043302 A1 | 5/2004 |
| WO | WO-2005102224 A2 | 11/2005 |
| WO | WO-2006028986 A2 | 3/2006 |
| WO | WO-2006060420 A1 | 6/2006 |
| WO | WO-2008076357 A1 | 6/2008 |

OTHER PUBLICATIONS

Opimesh 500 E—Extrapedicular Surgical Technique for Vertebral Stabilization, Spineology Inc., Jun. 24, 2003, p. 1-23.

Opimesh Surgical Mesh System, Technical Monograph, 2003 Spineology Inc., p. 1-10.

Cavity Creation Curette Set, Website of AO Foundation (http://www.aofoundation.org) printed Feb. 13, 2006.

Chiu et al. (2005) "Percutaneous Vertebral Augmentation and Reconstruction with an Intravertebral Mesh and Morcelized Bone Graft," The Internet Journal of Spine Surgery (website: http://www.ispub.

(56) References Cited

OTHER PUBLICATIONS com/ostia/index.php?xmlFilePath=journals/ijss/vol2n1/spine.xml) printed Oct. 4, 2007.
International Search Report and Written Opinion for PCT/US2007/025544, mailed on Apr. 23, 2008.
International Search Report and Written Opinion for PCT/US2007/025603, mailed on May 7, 2008.
International Search Report and Written Opinion for PCT/US2009/047614, mailed on Aug. 19, 2009.
Lam et al. (2005) "A Novel Percutaneous System for Bone Graft Delivery and Containment for Elevation and Stabilization of Vertebral Compression Fractures," Neurosurg Focus 18(3):1-7.
Vallejo et al. (2006) "Percutaneous Cement Injection into a Created Cavity for the Treatment of Vertebral Body Fracture," Clin. J. Pain. 22:182-89.
Verdult "Drilling Back Design and Development of a Directional Drilling Device/New Spinal Anchoring Technique" Dissertation, Delft University of Technology, The Netherlands, Dec. 1998.

* cited by examiner

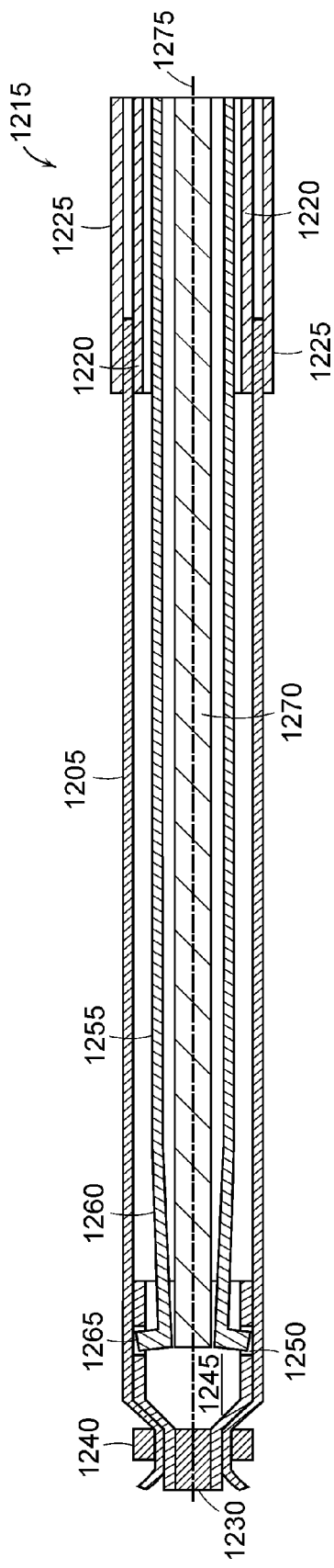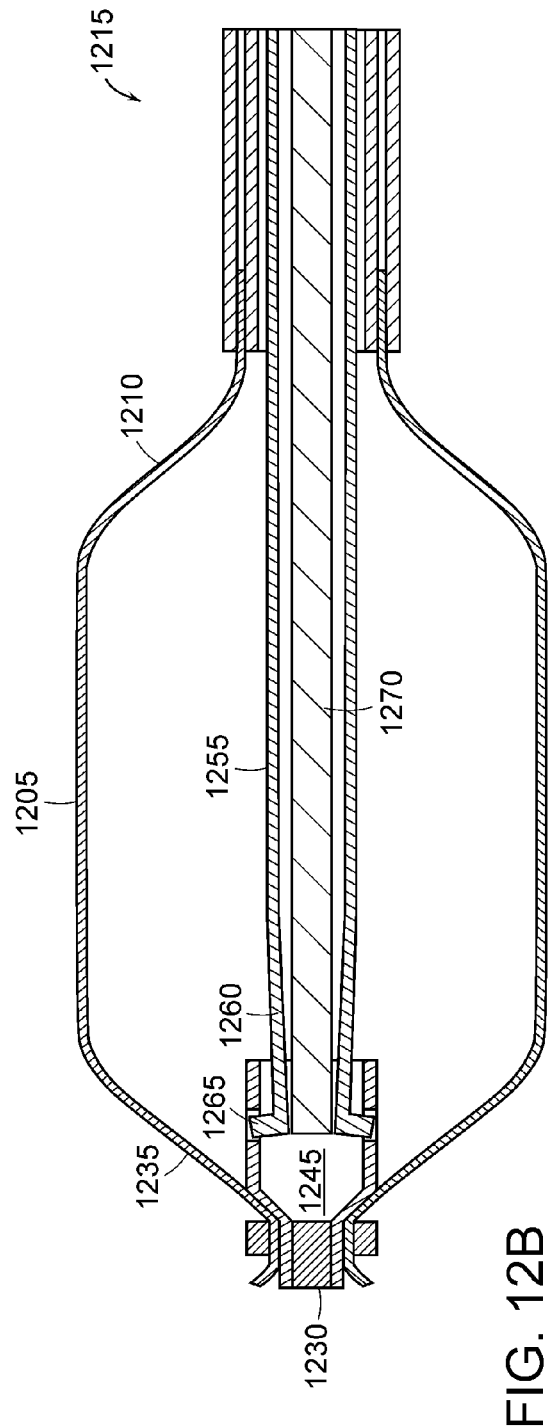
FIG. 12A
FIG. 12B

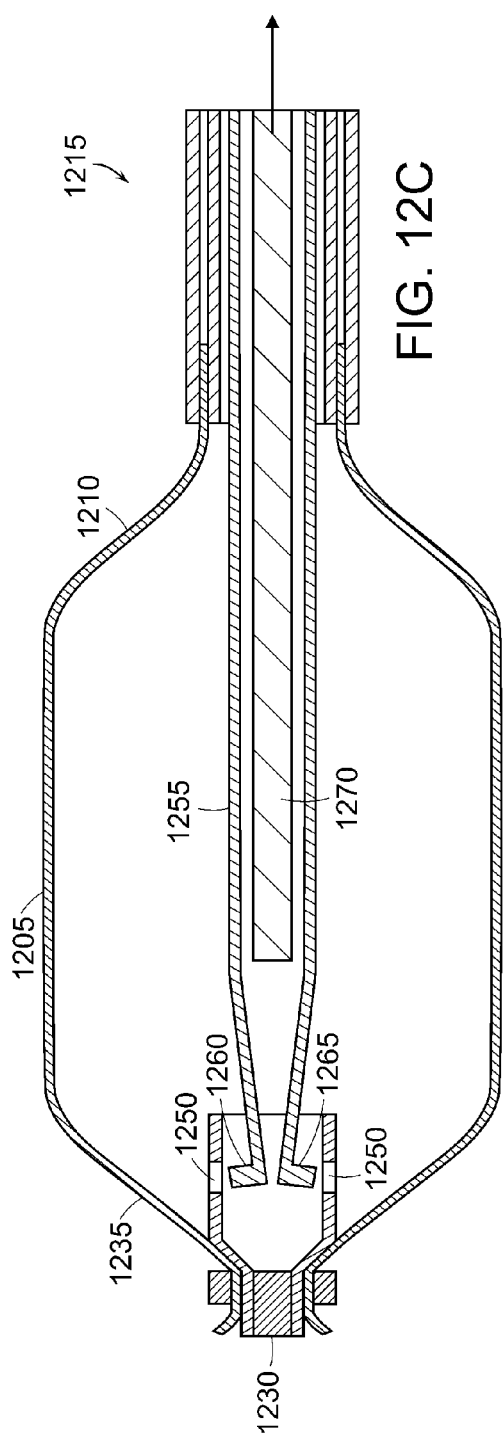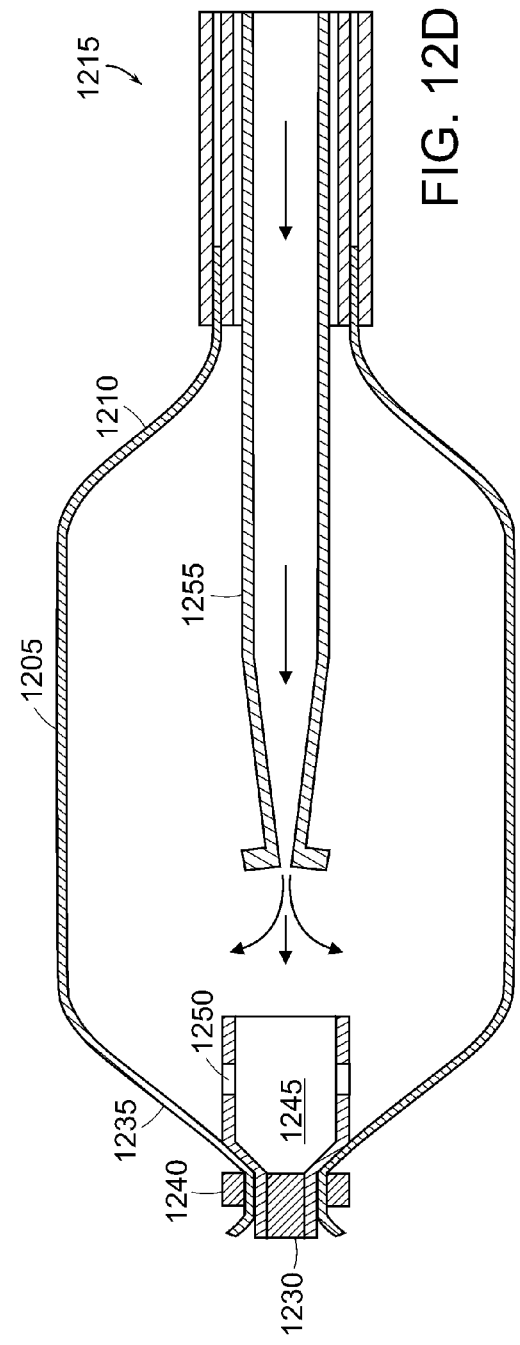

DELIVERY APPARATUS AND METHODS FOR VERTEBROSTENTING

CROSS-REFERENCE TO RELATED APPLICATIONS

This application is a continuation of U.S. patent application Ser. No. 11/957,039, filed Dec. 14, 2007, now U.S. Patent No. 7,909,873 and is related to U.S. patent application Ser. No. 11/957,022, filed Dec. 14, 2007, the disclosures of which are being incorporated herein by reference in their entireties. This application further claims priority to and the benefit of U.S. provisional patent application Ser. No. 60/875,114 filed Dec. 15, 2006, and U.S. provisional patent application Ser. No. 60/875,173 filed Dec. 15, 2006, the disclosure of which are being incorporated herein by reference in their entirety.

FIELD OF THE INVENTION

The present invention relates generally to the field of orthopedic devices to treat fractured bone in the spine, and more particularly to an orthopedic instrument and implant system that can be used to facilitate bone cement treatment of a vertebral compression fracture.

BACKGROUND OF THE INVENTION

There are many disease states that cause bone defects in the spinal column. For instance, osteoporosis and other metabolic bone conditions weaken the bone structure and predispose the bone to fracture. If not treated, certain fractures and bone defects of the vertebral body may produce intolerable pain, and may lead to the development of deformity and severe medical complications.

Bone weakening may also result from benign or malignant lesions of the spinal column. Tumors often compromise the structural integrity of the bone and thus require surgical stabilization and repair of defects with biocompatible materials such as bone grafts or cements. Bone tumors of the spine are relatively common, and many cause vertebral compression fracture.

More than 700,000 osteoporotic compression fractures of the vertebrae occur each year in the United States—primarily in the elderly female population. Until recently, treatment of such fractures was limited to conservative, non-operative therapies such as bed rest, bracing, and medications.

One surgical technique for treating vertebral compression fracture can include injecting or filling the fracture bone or bone defect with biocompatible bone cement. A relatively new procedure known as "vertebroplasty" was developed in the mid 1980's to address the inadequacy of conservative treatment for vertebral body fracture. This procedure involves injecting radio-opaque bone cement directly into a fracture void, through a minimally invasive cannula or needle, under fluoroscopic control. The cement is pressurized by a syringe or similar plunger mechanism, thus causing the cement to fill the void and penetrate the interstices of a broken trabecular bone. Once cured, the cement stabilizes the fracture and eliminates or reduces pain. Bone cements are generally formulations of non-resorbable biocompatible polymers such as PMMA (polymethylmethacrylate), or resorbable calcium phosphate cements which allow for the gradual replacement of the cement with living bone. Both types of bone cements have been used successfully in the treatment of bone defects secondary to compression fractures of the vertebral body.

One clinical issue associated with vertebroplasty is containment of the cement within the margins of the defect. For instance, an osteoporotic compression fracture usually compromises portions of the cortical bone creating pathways to cement leakage. Thus, there is a risk of cement flowing beyond the confines of the bone into the body cavity. Cement leakage into the spinal canal, for instance, can have grave consequences to the patient.

Yet another significant risk associated with vertebroplasty is the injection of cement directly into the venous system, since the veins within the vertebral body are larger than the tip of the needle used to inject the cement. A combination of injection pressure and inherent vascular pressure may cause unintended uptake of cement into the pulmonary vessel system, with potentially disastrous consequences including embolism to the lungs.

One technique which has gained popularity in recent years is a modified vertebroplasty technique in which a "balloon tamp" is inserted into the vertebral body via a cannula approach to expand or distract the fractured bone and create a void within the cancellous structure. Balloon tamps are inflated using pressurized fluid such as saline solution. The inflation of a balloon membrane produces a radial force on the bone and forms a cavity in the bone. When deflated and removed, the membrane leaves a cavity that is subsequently filled with bone cement. The formation of a cavity within the bone allows for the injection of more viscous cement material which may be relatively less prone to leakage.

In certain instances, such as the treatment of acute or mobile fractures, the balloon is also effective at "reducing" the fracture and restoring anatomic shape to a fractured body. In particular, balloon dilatation in bone is maximally effective if the balloon device is targeted inferior to, or below, the fracture plane. In this instance, the balloon dilatation may distract, or lift, a fracture bone fragment, such as the vertebral body endplate.

In other instances, such as chronic or partially healed fractures, balloons are less effective at "reducing" the fracture because radial forces are insufficient. Often the bone in an incompletely healing fracture is too dense and strong, and requires more aggressive cutting treatment, such as a drill or reamer tool to create a sufficient cavity. In these more challenging cases, the ability to inject bone cement into a cavity created by a balloon or a reamer in the vicinity of the fracture is typically sufficient to stabilize the bone and relieve pain, even in the absence of fracture reduction.

One limitation to the use of such methods has been the difficulty in targeting the location at which the cavity should be created. Known techniques require access to the vertebral body using straight cutting and reaming tools which are only able to access a limited region of the vertebral body being treated, generally only within one side of the vertebral body. A cavity created using these techniques can only treat one side of a vertebral body being targeted, resulting in an uneven distribution of bone cement that cannot completely stabilize the vertebral body. As a result, multiple entry points on different sides of the vertebral body are generally required in order to provide a symmetrical distribution of bone cement around a central axis of the vertebral body. These multiple entry points significantly increase the time necessary for the procedure, the portion of the body being treated, and the amount of bone cement being injected, and as such can significantly increase the risks associated with treatment of a patient.

SUMMARY OF THE INVENTION

The present invention is directed towards novel methods and devices for preparing a cavity in bone, deploying a cement-directing stent device, and injecting bone cement into the device. The methods and devices disclosed herein can allow a cavity to be created in a vertebral body along a curvilinear pathway, allowing for a substantially symmetrical distribution of bone cement over a central vertical axis of a vertebral body. This can allow a vertebral body to be successfully and completely stabilized from a single surgical access point and using a single stent device.

One aspect of the invention can include a method of deploying a stent within an enlarged curvilinear void created in a bony structure. The method can include the steps of: inserting a distal end of a stent delivery system through a cannula and into a curvilinear void created in a bony structure, deploying a self-expanding cement-directing stent within the curvilinear void, wherein the self-expanding stent is releasably attached to the distal end of the stent delivery system, attaching a cement injecting syringe to the proximal end of the stent delivery system, injecting cement through the stent delivery system and into the stent, terminating the cement injection when the volume of cement injected exceeds the interior volume of the expanded stent, and releasing the stent from the stent delivery system.

In one embodiment, the stent delivery system can include at least one of a proximal deployment mechanism, an internal flexible guidewire, and an internal flexible tube, such as a polymer extrusion. The self-expanding cement-directing stent can include a multifilament braided, polymer impregnated, self-expanding, cement-directing stent collapsed on the distal end of the guidewire and restrained in a collapsed condition by a tubular polymer sheath. The self-expanding cement-directing stent can be deployed by slideably uncovering the tubular sheath to release and expand the stent within an enlarged curvilinear void. The self-expanding cement-directing stent can be alternatively or further deployed by removing the internal flexible guidewire and/or the polymer extrusion.

Alternatively, another method of stent deployment eliminates the need for the tubular sheath. The self-expanding cement-directing stent is maintained in a collapsed state solely by the internal flexible guidewire and/or the polymer extrusion. Once positioned in the enlarged curvilinear void, deployment of the self-expanding cement-directing stent can be accomplished solely by removing the internal flexible guidewire and/or the polymer extrusion.

In one embodiment, the self-expanding cement-directing stent can be connectably attached to the proximal deployment mechanism by a hollow tube assembly. The stent can be released by actuating the proximal deployment mechanism.

One aspect of the invention can include a method of deploying a stent within an enlarged curvilinear void created in a bony structure. The method can include the step of inserting a stent catheter assembly into an enlarged curvilinear void through a cannula and into the curvilinear void created in a bony structure, wherein the stent catheter assembly can include a proximal deployment mechanism, an internal flexible guidewire, a multifilament braided, polymer impregnated, self-expanding, cement-directing stent collapsed on the distal end of the guidewire and restrained in a collapsed condition by a tubular polymer sheath, and connectably attached to the distal end of the deployment mechanism by a hollow tube assembly.

The method can further include the steps of deploying the self-expanding cement directing stent by slideably uncovering the tubular sheath to release and expand the stent within the enlarged void within the bony structure, removing the internal flexible guidewire, attaching a cement filled cement injecting syringe to the proximal deployment mechanism, injecting cement into the proximal deployment mechanism through the hollow tube assembly into the stent, pressurizing the cement to cause the complete filling of the stent interior, terminating the filling when the volume of cement injected exceeds the interior volume of the expanded stent, and releasing the stent from the hollow tube assembly.

In one embodiment, the self-expanding cement-directing stent can include a multifilament braided, polymer impregnated, self-expanding, cement-directing stent. In one embodiment, the stent delivery system can include a handle and an elongate shaft. The stent can be releasably attached to a distal end of the elongate shaft. In one embodiment, the stent is further releasably attached at a distal end thereof, The stent can be released by actuating a user control mechanism on the handle. The elongate shaft can include at least one of an inner shaft, an outer shaft, a tubular sheath, a flexible guidewire, and an internal polymer extrusion.

In one embodiment, prior to the deploying step the self-expanding cement-directing stent is collapsed on a distal end of at least one of the inner shaft, the guidewire, and the polymer extrusion. The self-expanding cement-directing stent can be deployed by retracting at least one of the inner or outer shaft, the flexible guidewire, and the polymer extrusion.

In one embodiment, prior to the deploying step the self-expanding cement-directing stent can be restrained in a collapsed condition by the tubular sheath. The self-expanding cement-directing stent can be deployed by slideably retracting the tubular sheath to allow the stent to self-expand within the enlarged curvilinear void. In one embodiment, the deploying step includes actuating a rotating cam mechanism.

The invention is also drawn to stent delivery systems and components thereof adapted for use with any of the methods described above.

Another aspect of the invention can include a stent delivery system for deploying a stent within an enlarged curvilinear void created in a bony structure. The stent delivery system can include a handle and an elongate shaft adapted to releasably hold a self-expanding cement-directing stent at a distal end thereof. The elongate shaft can include a sheath and at least one of an inner and an outer shaft. The stent delivery system can also include at least one user control mechanism adapted to deploy the stent.

In one embodiment, the at least one user control mechanism includes a rotating cam mechanism. Actuating the rotating cam mechanism can retract the sheath towards the handle. In one embodiment, actuating the rotating cam mechanism simultaneously extends the distal end of at least one of the inner and the outer shaft away from the handle.

In one embodiment, a distal end of the handle can include an interface element adapted to releasably engage at least a portion of proximal end of a cannula. The stent delivery system can also include a stent release mechanism adapted to release the stent from the elongate shaft.

Another aspect of the invention can include a user control mechanism for a stent delivery device. The user control mechanism can include a support element, at least one cam shaft helically positioned on the support element, a linear support sleeve, and at least one pin engaging the cam shaft and the linear support sleeve. The cam shaft and the linear support sleeve force the pin linearly along an axial extent of the user control mechanism upon a rotation of the support element.

In one embodiment, the at least one pin is attached to an elongate shaft extending from a distal end of the user control element. The elongate shaft can include at least one of an inner shaft, an outer shaft, and a sheath.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 12A is a schematic sectional side view side view of a releasable attachment mechanism attached at a distal end of a collapsed stent, in accordance with one embodiment of the invention;

FIG. 12B is a schematic sectional side view of the releasable attachment mechanism of FIG. 12A after expansion of the stent;

FIG. 12C is a schematic sectional side view of the releasable attachment mechanism of FIG. 12A after detachment from the distal end of the stent; and FIG. 12D is a schematic sectional side view of the releasable attachment mechanism of FIG. 12A injecting filler material into the stent after removal of the inner rod.

DETAILED DESCRIPTION OF THE INVENTION

Figure 1A:
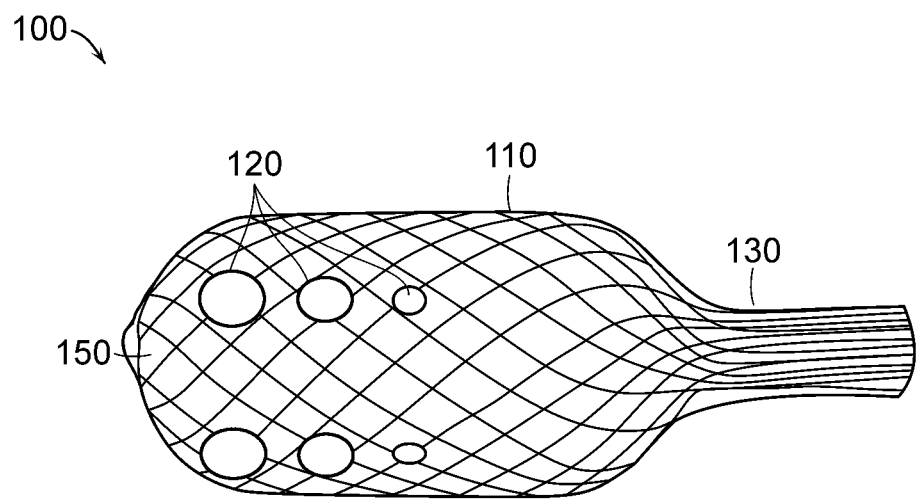
FIG. 1A is a schematic side view of a stent including a plurality of holes, in accordance with one embodiment of the invention.
Figure 1B:
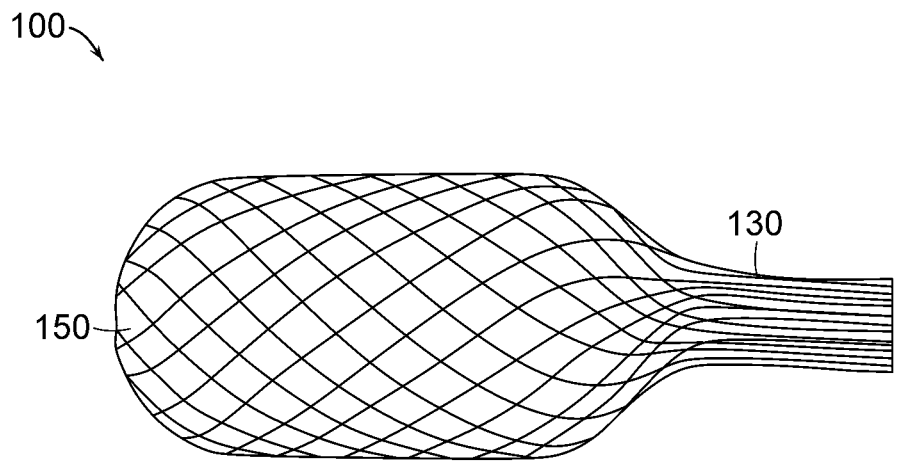
FIG. 1B is another schematic side view of the stent of FIG. 1A.
Figure 1C:
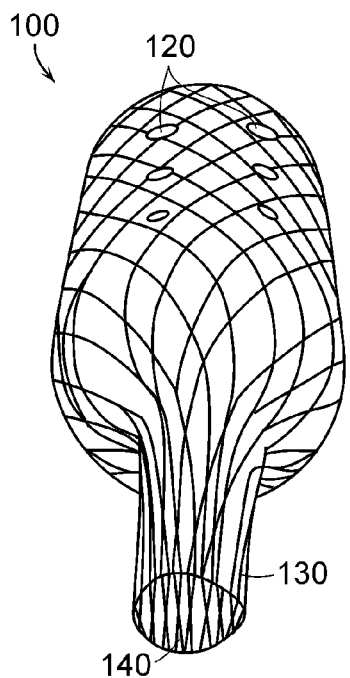
FIG. 1C is a schematic rear perspective view of the stent of FIG. 1A, showing the plurality of holes.
Figure 1D:
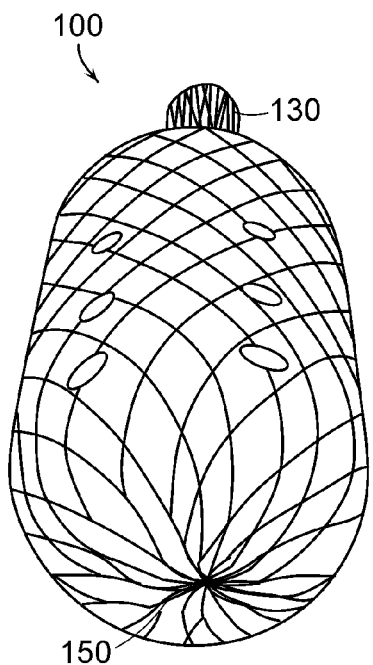
FIG. 1D is a schematic front perspective view of the stent of FIG. 1A, showing the plurality of holes.
Figure 1E:
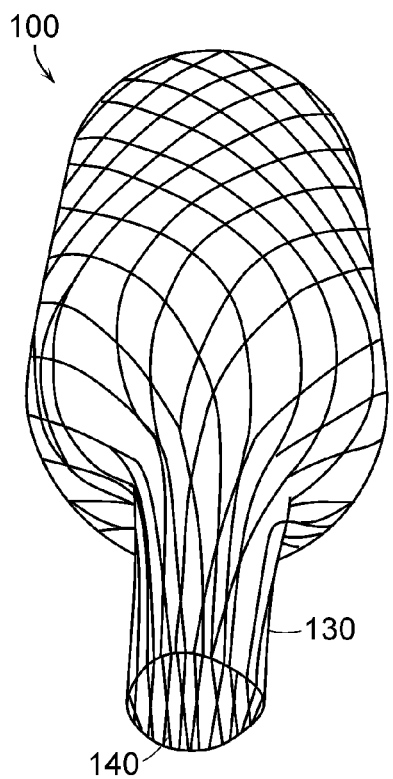
FIG. 1E is another schematic rear perspective view of the stent of FIG. 1A.
Figure 1F:
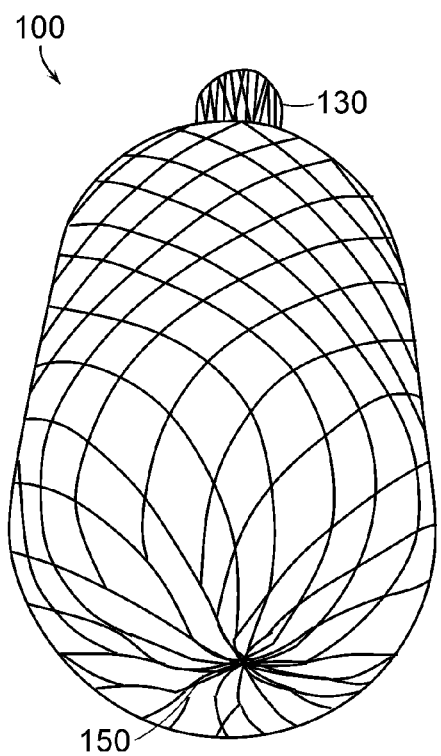
FIG. 1F is another schematic front perspective view of the stent of FIG. 1A.

The present invention discloses methods and apparatus for introducing a stent into a curvilinear or other shaped cavity created within the cancellous bone of a fractured vertebral body or other bony structure. The invention also discloses methods and apparatus for injecting cement into the stent and into the surrounding cancellous bone through positioned exit holes in the stent.

The methods and apparatus disclosed herein allow for a covered stent to be safely inserted into the vertebral body through the same entry profile as current vertebral compression fracture treatments. Once in place, the delivery apparatus can direct cement into the stent and through the designated holes into the vertebral body. This can allow for the controlled flow of cement away from the spinal canal and towards the anterior side of the vertebral body. Unlike cardiovascular stent delivery systems, the delivery systems disclosed herein have a positive attachment to the stent for cement injection and stent placement adjustability, thus increasing the stability, controllability, and safety of the system during surgical procedures.

In one embodiment of the invention, expansion of a stent in response to retraction of an outer sheath covering the stent, and maintaining it in a collapsed configuration, is performed in an orthopedic rather than cardiovascular environment. In one embodiment, the delivery system may have certain features that exhibit some similarity to cardiovascular and endoscopic medical device designs, but may also have several mechanical additions specially designed and configured for orthopedic compatibility.

In one embodiment, the delivery system is configured to compensate for stent foreshortening in a closed cavity environment. Foreshortening of a stent occurs when a stent is expanded from a radially collapsed configuration to a radially expanded configuration, with the expansion resulting in a reduction in length as the diameter of the stent is increased. This length reduction results in the expanded stent being retracted back from the distal wall of the cavity in which it is deployed, which in turn results in the expanded stent failing to completely fill the cavity in which it is deployed. The delivery systems disclosed herein therefore differ from the usual stent delivery systems that are used in vascular or duct environments where longitudinal space is available to allow foreshortening.

In one embodiment, the stent can be attached to the distal tip of the delivery system and is not automatically released from the device during stent expansion. As a result, physicians are able to pull the stent out of the vertebral body during the surgical procedure, compress, recover with the outer sheath and redeliver the stent if the physician is not satisfied with the original placement. This recovery and redeployment can greatly increase the chances of correctly placing the stent in the most advantageous, and safe, position within a patient.

In one embodiment of the invention, the delivery system has the ability to retract an outer sheath maintaining the stent in a collapsed configuration from a side portal in order to minimize the length of the delivery system. Cement injection back pressures significantly increase with longer cement injection channels. By incorporating a slit into the outer sheath to allow the outer sheath extrusion to pass over the shafts of the delivery system and be pulled sideways or linearly through the handle, the overall delivery system length can be reduced. This allows the cement to travel a shorter distance to fill the stent, and therefore reduces the injection pressure required to inject cement into the stent at substantially zero pressure. This reduction in injection pressure can increase the usability of the delivery system, while reducing the potential for failure of the injection process, and increasing the safety of the system.

In one embodiment, the method of cement injection through the delivery systems disclosed herein may provide a safer and more efficient means of treating a vertebral compression fracture than current vertebral compression fracture treatments. In one embodiment, cement may be initially injected by a syringe through the inner shaft of the delivery system. The delivery system can direct the cement straight into the stent and through the designated outlet holes in the stent into the surrounding cancellous bone. Once injection with a syringe becomes difficult, for example as a result of the cement curing, a solid piston can be inserted into the inner shaft to deliver more cement. The inner lumen of the delivery system can, in one embodiment, hold approximately 1.5 cc of cement from the proximal to the distal end. The cement piston can also be used to completely clear the inner shaft of cement to prevent cement back flow out of the pedical. With the delivery system and stent attachment at the distal tip of the delivery system, cement injection becomes more controlled than in more traditional techniques of vertebroplasty and kyphoplasty.

Stent

In one embodiment of the invention, a stent can include a multifilament co-braided shaped structure and a self-expanding structure composite which is collapsible to an elongated tubular shape suitable to fit within a tubular sheath assembled to a novel delivery catheter. The outer wall of the stent can be impregnated in preferred regions with a polymer to form a thicker, relatively less permeable wall. The polymer impregnated co-braided wall is further perforated with holes or slots in preferred locations. An example cement directing stent for use with this invention is disclosed in U.S. Patent Publication No. 2005/0261781 A1 to Sennett et al., the disclosure of which is incorporated herein by reference in its entirety. The stent geometry is optimized to fit within a reamed or balloon-expanded cavity located approximately within the anterior ⅔ of a vertebral body. The cavity is formed by a sequential method using a number of specifically designed instruments. An example stent 100 is shown in FIGS. 1A-1F.

In one embodiment of the invention, the stent 100 can be sized to substantially conform to the dimensions of a predetermined cavity created within a vertebral body. The stent 100 can be configured to be collapsible, thus allowing delivery of the stent 100 through a relatively small diameter access cannula. The stent 100 can also have a self-restoring shape, allowing the stent to automatically expand to its original shape, corresponding substantially with the dimensions of the cavity into which it is inserted, without the need for inflation of the stent 100 by the injection of filler material or other fluids or substances. In one embodiment, the stent 100 may be self-restoring to an expanded configuration, at least because it is constructed, at least in part, from a shape-memory material, such as, but not limited to, nitinol. The stent 100 may be constructed, at least in part, as a braided structure 110.

In one embodiment, expansion of the stent 100 does not generate a distraction force on the end plates of the vertebral body and does not compact the interior cancellous bone structure of the vertebral body. Upon expansion of the stent 100 within the vertebral body, filler material (such as bone cement) can be injected into the stent 100 to at least partially fill the interior of the stent 100. In one embodiment, the injection of filler material does not substantially alter the shape and dimensions of the stent 100, other than to conform the stent, if necessary, to the shape of the cavity in which it is disposed.

In one embodiment of the invention, the wall of the stent may include at least one hole 120 or permeable region allowing filler material to leave the interior of the stent 100 and enter the vertebral body. The at least one hole 120 or porous region can allow for the controlled and directed distribution of filler material within the vertebral body. The wall of the stent 100 may include a plurality of holes of various sizes and/or a plurality of regions of differing permeability, allowing for a greater or lesser escape of filler material in different directions. The wall of the stent 100 may also include at least one baffle or other non-permeable region preventing the escape of filler material in certain directions. In general, the total cross-sectional area of the holes exceeds that of a cement inlet hole 140, to prevent excess back pressure or buildup of pressure in the interior of the stent.

In one embodiment, the stent 100 may have a proximal region 130 that is configured to be releasably mounted to a delivery system and includes the inlet hole 140 to allow for the injection of cement. The stent 100 can also have a closed distal region 150 to be positioned away from the delivery system and to be placed against the distal end of the cavity in which it is placed.

In one embodiment, the method of treating the patient may involve external reduction by extension, i.e. physical manipulation of the patient when placing the patient on the operating table before treatment of the vertebral fracture site. The method of treating the patient can also involve stabilizing the vertebral body, not distracting the upper and lower end plates using the stent as an expansion device.

Delivery System

Figure 2A:
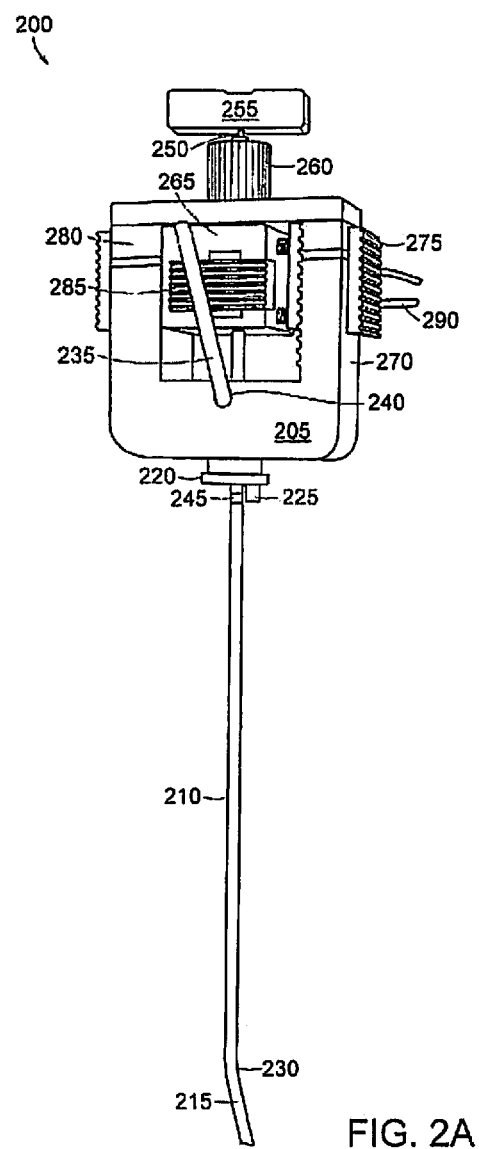
FIG. 2A is a schematic plan view of a delivery system for a stent, in accordance with one embodiment of the invention.

An example of a delivery system can be seen in FIG. 2A. The delivery system 200 can include a handle portion 205 at a proximal end, and a hollow elongate shaft 210 extending towards a distal end. A stent 215 can be releasably held at the distal end of the hollow elongate shaft 210.

In one embodiment of the invention, the delivery system 200 can be configured to releasably couple to a cannula that is inserted percutaneously from the posterior approach through the outer tissue of a patient and anchored into the bone of the vertebral body to a suitable depth. The hollow elongate shaft 210 can be configured to slidably extend through the cannula such that the stent 215 protrudes from the distal end of the cannula and into a curvilinear cavity formed within the vertebral body. The stent may be configured to extend at a specific angle, or along a predetermined arc, to conform to the axis of the cavity. In an alternative embodiment, the stent may extend straight out from the distal end of the hollow elongate shaft 210.

The flexibility and resiliency of the stent is well adapted for use in cavities having a variety of shapes, including curvilinear, cylindrical, tapered, conical, etc. The stent may be flexible, such that it may be deflected by the walls of the cavity and therefore conform substantially to the curvature or shape of the cavity when inserted. In a further alternative embodiment, the cavity may extend straight out from the distal end of the cannula, and no curvature or deflection of the stent is required for correct insertion of the stent into the cavity.

In one embodiment, a flange 220 and key 225 may be fitted to the handle portion 205 of the delivery system 200 at the proximal end of the hollow elongate shaft 210. The flange 220 may enable the delivery system to be releasably locked to the cannula to ensure stability of the delivery system 200 during the procedure. The key 225 may be configured to mate with a slot in the cannula to ensure that the delivery system 200 is inserted into the cannula in the correct circumferential orientation. In an alternative embodiment, the delivery system 200 may include a locking mechanism, latch, or other appropriate means of releasable engagement with the cannula. In a further alternative embodiment, no means of locking the delivery system 200 to the cannula may be required.

In one embodiment, a sheath 230 may be used to releasably maintain the stent 215 in a collapsed configuration during insertion through the cannula and into the cavity. The collapsed configuration may be substantially the same diameter as the diameter of the hollow elongate shaft 210 (i.e. a diameter configured to fit slidably through the cannula). The sheath 230 may be a hollow elongate flexible tube of plastic, fabric, wire mesh, composite, metal or other appropriate material, that can slideably extend over the hollow elongate shaft 210 and stent 215 to hold the stent 215 at a set diameter substantially equal to the diameter of the hollow elongate shaft 210.

The proximal end 235 of the sheath 230 may extend through an exit hole 240 in the handle 205 of the delivery system 200. An elongate slot may be inserted in a portion of the proximal end 235 of the sheath 230 to allow the sheath 230 to be pulled out through the exit hole 240 without tearing. In one embodiment, a handle may be placed on the end of the sheath 230 to assist in pulling the sheath 230 out through the exit hole 240.

In use, the sheath 230 is slid over the hollow elongate shaft 210 and stent 215 to hold the stent 215 in a collapsed configuration. Once the stent 215 has been inserted through the cannula and into the cavity, the sheath 230 can be pulled back through the exit hole 240 in the handle 205. This retracts the sheath 230 back along the hollow elongate shaft 210 and off the stent 215. The stent 215 is then free to self-expand to its original shape, which may, in one embodiment, conform substantially with the shape of the curvilinear cavity. In one embodiment, a marking 245 may be placed on the sheath 230 near the proximal end 235 to indicate to a user when the sheath 230 has been retracted far enough to uncover the stent 215.

In addition to the sheath 230, or possibly in place of the sheath 230, a polymer extrusion and/or a flexible guidewire 250 may be inserted through the handle 205 and hollow elongate shaft 210 to provide an internal force to extend the distal end of the stent 215 and assist in holding the stent 215 in a collapsed, or partially collapsed, configuration. The polymer extrusion may be an elongated hollow polymer shaft made of any flexible polymer such as PEBAX, Nylon PET or PTFE. The flexible guidewire 250 may be an elongate solid or hollow rod of stainless steel, aluminum, plastic, or another appropriate material, that may slideably extend through the hollow elongate shaft 210 of the delivery system 200, with the distal end of the flexible guidewire 250 abutting against the interior distal end of the stent 215 to force the stent forward.

In one embodiment, the flexible guidewire 250 may also include a guidewire handle 255 that can assist the user in pulling and pushing on the guidewire 250 as required. A mounting element 260 may be releasably connected to the end of the handle 205 with a bayonet retention feature or other attachment feature and through which the flexible guidewire 250 passes. The mounting element 260 may also be connected to the polymer extrusion that extends down to the stent 215 and is disposed coaxially between the flexible guidewire 250 and the hollow elongate shaft 210 of the delivery system 200. This extrusion may be used, for example, to provide a smooth, low friction boundary between the guidewire 250 and the hollow elongate shaft 210. The polymer extrusion may be of a length such that the extrusion also assists in maintaining the stent 215 in a collapsed configuration prior to insertion and deployment in the cavity. The mounting element 260 may be used to cover a luer lock, or other mounting feature, that may be used to releasably hold a syringe once the inner core assembly (i.e., polymer extrusion and guidewire 250) has been removed.

The inner core assembly (i.e., polymer extrusion and guidewire 250) may provide multiple functions for the delivery system 200. For example, the inner core assembly (i.e., polymer extrusion and guidewire 250) may be used to assist in maintaining the stent 215 in a collapsed configuration prior to insertion and deployment in the cavity. The inner core assembly (i.e., polymer extrusion and guidewire 250) may also be used to counteract any foreshortening of the stent 215 that may occur during expansion.

In one embodiment, a sliding mechanism 265 can also be used to counteract foreshortening of the stent 215 as a result of expansion within the cavity. The sliding mechanism may be fixedly coupled to the hollow elongate shaft 210 of the delivery system 200, and be slidably coupled to the handle 205 of the delivery system 200. By sliding the sliding element 265 forward, the entire hollow elongate shaft 210 and attached stent 215 can be pushed forward, thus pushing the distal end of the expanded stent 215 towards the distal end of the cavity. After the stent 215 has been pushed to the end of the cavity, the sliding element 265 can be slid backwards by a small amount to counteract any foreshortening of the proximal end of the stent 215 that may result from the pushing process. A releasable locking mechanism 270, including a spring mounted locking element 275, can be used to ensure that the sliding element 265 is locked in place when not needed. In one embodiment, markings may be placed on the handle 205 to indicate the length of travel of the sliding element 265.

Once a stent 215 has expanded and been correctly positioned within a cavity, the stent 215 may be filled with cement, cement analogue, or other filler material, by fitting a syringe to the luer lock, or other locking mechanism at the proximal end of the hollow elongate shaft 210, after the inner core assembly (i.e., polymer extrusion and guidewire 250) has been removed. The cement can then flow through the hollow elongate shaft 210 and into the interior of the stent 215, after which it can flow into the vertebral body through the carefully positioned holes in the stent 215.

Once the stent has been filled, the stent can be released from the delivery system 200 and the system removed from the patient. A locking mechanism 280 may be included in the handle 205 of the delivery system 200 to releasably hold the stent 215 to the hollow elongate shaft 210. The locking mechanism 280 may be attached to an elongate element that is attached at its distal end to the proximate end of the stent 215. The locking mechanism 280 may also include a slider 285, or a switch, clasp, or other user interface element, to unlock the stent 215 from the elongate element and/or hollow elongate shaft 210 once the stent has been correctly positioned and filled. In one embodiment, a pin 290 may be removably inserted into the locking mechanism 280 to ensure that the stent 215 is not released accidentally.

It should be noted that at all steps of a method using the above-identified delivery system 200, medical imaging techniques, such as fluoroscopy, may be used to image the interior of the vertebral body and confirm the location and status of the stent 215, cement, and cavity.

Figure 2B:
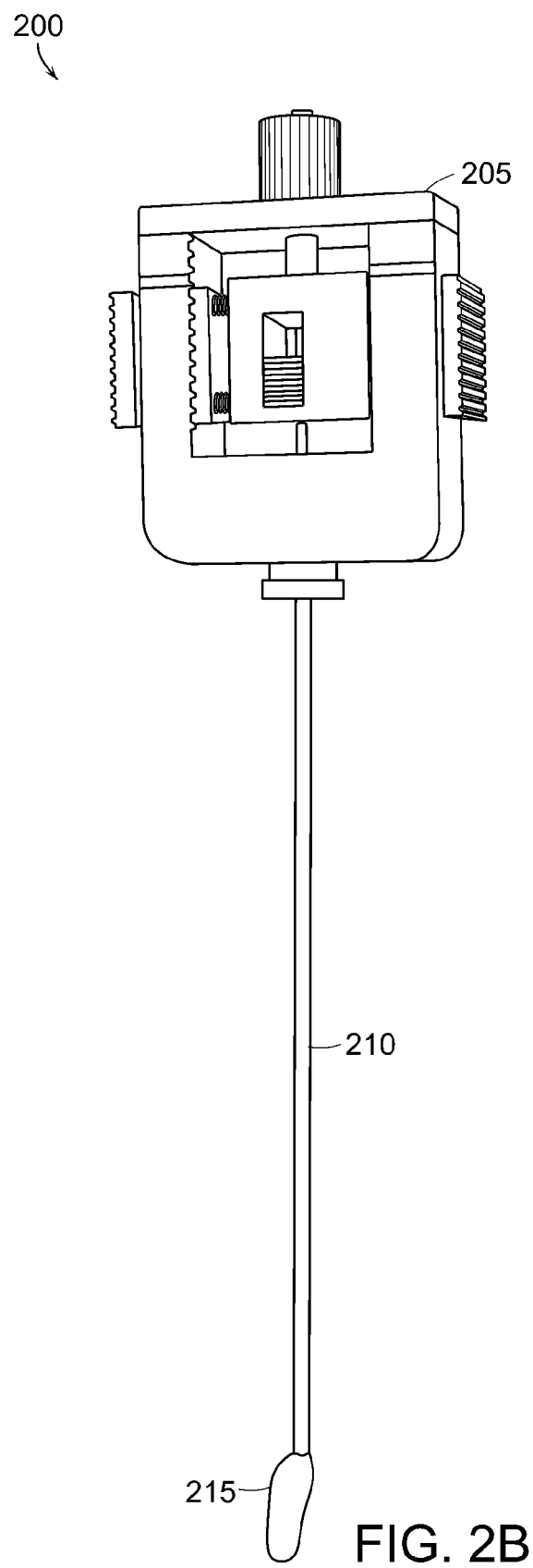
FIG. 2B is another schematic plan view of the delivery system of FIG. 2A.
Figure 2C:
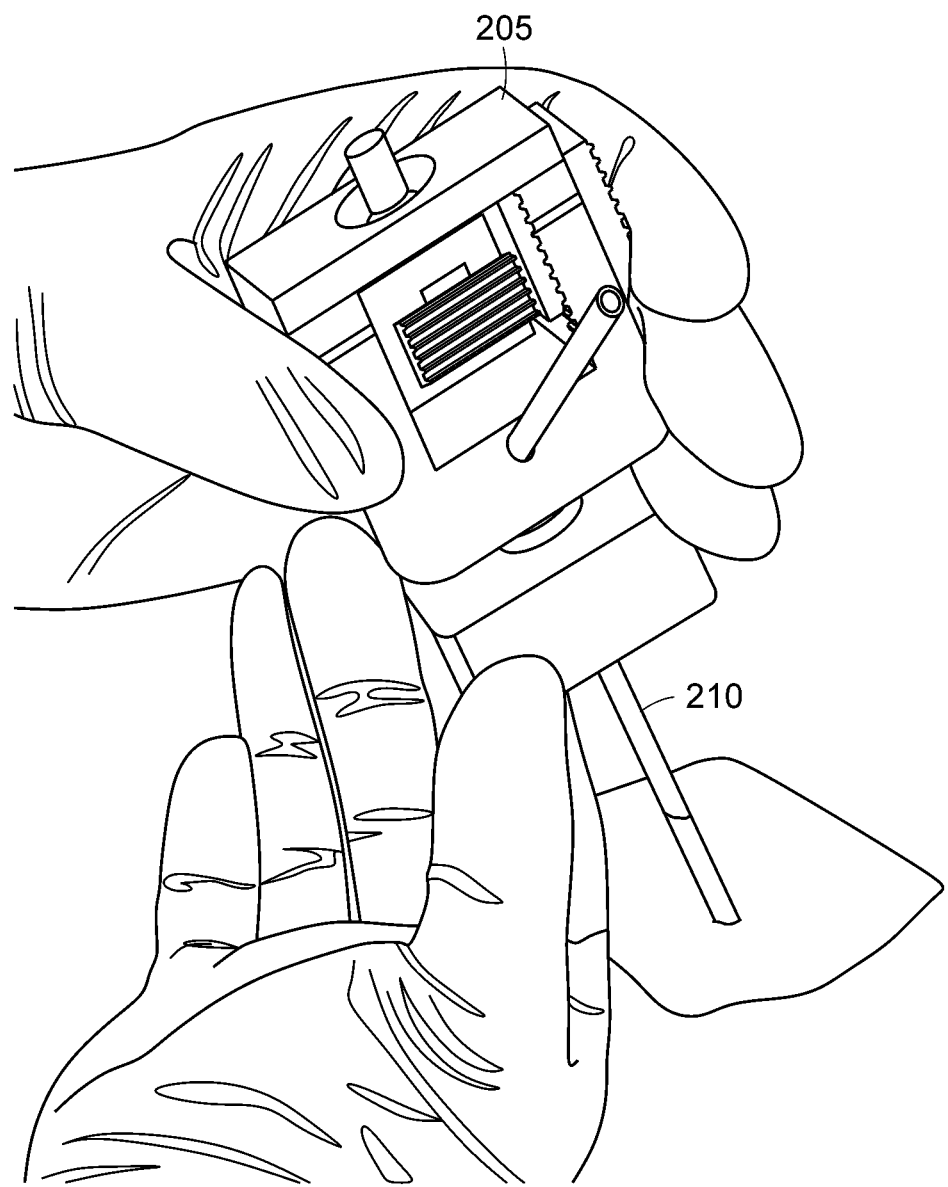
FIG. 2C is an illustration of a delivery system inserted in a patient, in accordance with one embodiment of the invention.
Figure 2D:
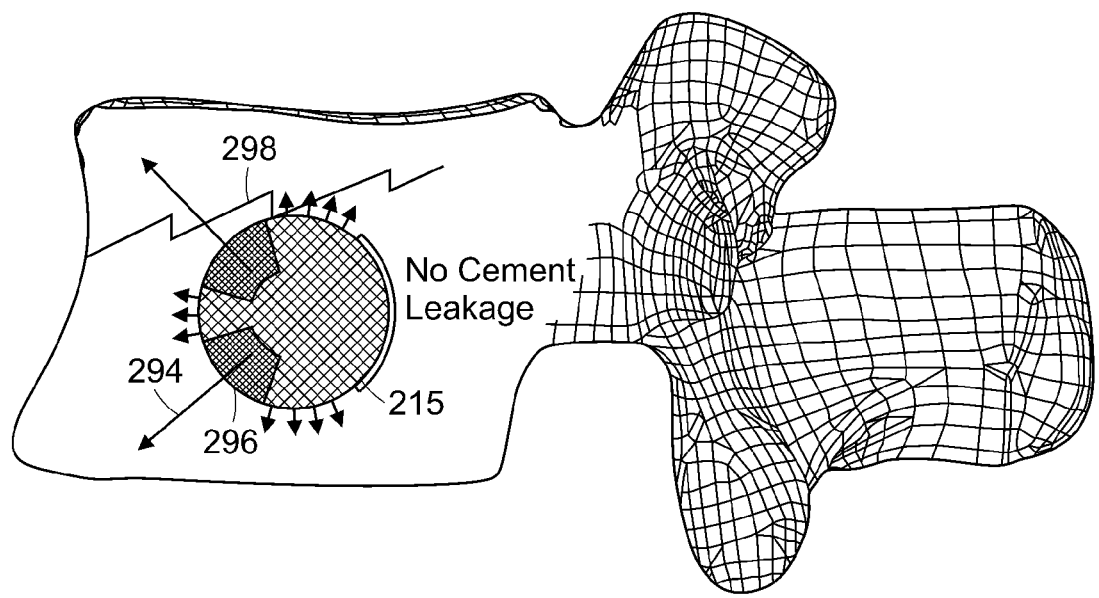
FIG. 2D is a schematic side view of a cement filled stent inserted in a vertebral body, in accordance with one embodiment of the invention.

An example a delivery system 200 with the sheath 230 retracted and the stent 215 expended is shown in FIG. 2B. An example of this delivery system 200 inserted into a patient can be seen in FIG. 2C. A cross-section of a cement filled stent 215 inserted into a vertebral body 292 is shown in FIG. 2D. In this figure, large arrows 294 indicate the direction of the cement leaving through holes 296 in the stent 215 in order to stabilize a fracture 298. Small arrows correspond to areas of lower permeability of the stent 215, through which nominal amounts of cement leave the stent 215 to further anchor the stent 215 and fill any remaining voids in the cavity.

Method of Use

An embodiment of the invention can include a method of using the delivery systems described herein to insert and deploy a stent device into a cavity created in a vertebral body. The cavity may be a curvilinear cavity. In an alternative embodiment, the cavity may be of any appropriate size and shape, with a stent selected to be configured to substantially conform to the size and shape of the cavity created.

In one embodiment of the invention, a procedure for using the devices disclosed herein can be used to produce a curvilinear cavity within a vertebral body, and place a stent within the cavity created within the vertebral body. The stent can be a self-expanding, covered stent that allows interdigitation and prevents leakage of bone cement in undesired directions. In one embodiment, a single stent can be placed at a mid-line location of a vertebral body, rather than placing multiple stents on either side of the mid-line, thus reducing the time and fluoroscopy exposure require during a surgical implantation procedure.

In one embodiment, the method of creating a cavity for within a vertebral body, or other bony body, can include first creating a posterior pathway to the vertebral body, using a extrapedicular or intrapedicular approach, with a Jamshidi needle and/or K-wire. This may be performed, for example, using a dual C-arm technique to place and medialize the Jamshidi needle/K-wire to the fullest extent.

A working channel and trocar assembly can then be inserted along the pathway created by the Jamshidi needle/K-wire. This can be performed, for example, by locking the trocar into the working channel, inserting the working channel into the pathway, and tapping the assembly into place until the distal tip of the trocar and working channel extends, in one embodiment, 1-3 mm beyond the posterior wall of the vertebral body. The trocar can then be removed, leaving the open working channel in place.

A curved pathway through the vertebral body can then be created using a curved drill. This may be achieved using any of the drill arrangements described herein. In one embodiment, the drill depth markings at the user interface are set to "0" mm prior to insertion into the working channel. The drill can then be locked into the working channel with the key facing in the medial direction, thus ensuring the correct direction of curvature of the drill within the vertebral body. The handle of the drill can then be rotated to advance the drill tip into the vertebral body, with fluoroscopy, or some other appropriate technique, used to determine when the desired depth of penetration is achieved. The drill can then be removed and the depth markings on the user interface recorded. In one embodiment, the drill tip is oriented in the contralateral anterior quadrant of the vertebral body, thus assuring proper cavity positioning and bilateral cement filling.

In one embodiment, a larger cavity can then be created within the vertebral body by reaming out the hole created by the curved drill with a curved reamer. This may be achieved, for example, by first setting the depth markings on the user interface of the reamer to match those recorded for the drill depth, thus assuring that the reamer is positioned correctly within the vertebral body. The reamer can then be advanced fully into the pathway created by the drill and locked into the working channel, with the position of the reamer confirmed using fluoroscopy or some other appropriate technique. The blade of the reamer can then be opened, for example by rotating a portion of the handle of the reamer, and reaming can be carried out by rotating the handle. In one embodiment, the reamer may be stopped approximately 1-3 mm before approaching the distal tip of the working channel, with the position confirmed by fluoroscopy, or some other appropriate technique. The blade can then be closed (for example by rotating a portion of the handle in the opposite direction), and the reamer removed. In one embodiment, due to blade deflection, the cavity created by the reamer can have a slight taper from the distal end to the proximal end.

Once a cavity has been created, a stent delivery system can be locked into the working channel to correctly position a stent within the vertebral body. Once the stent has been positioned, a sheath covering the stent can be removed to deploy and expand the stent, and cement can be injected into the stent by attaching a syringe to the proximal end of the delivery system. The desired amount of cement can be injected into the stent with fluoroscopy, or some other appropriate technique, being used to monitor the flow of cement into the stent. Once the requisite amount of cement has been injected, the stent can be released from the delivery system and the delivery system removed from the working channel, thus leaving the stent in place within the vertebral body. The working channel can then be removed and the access pathway sutured or otherwise closed.

Figure 3A:
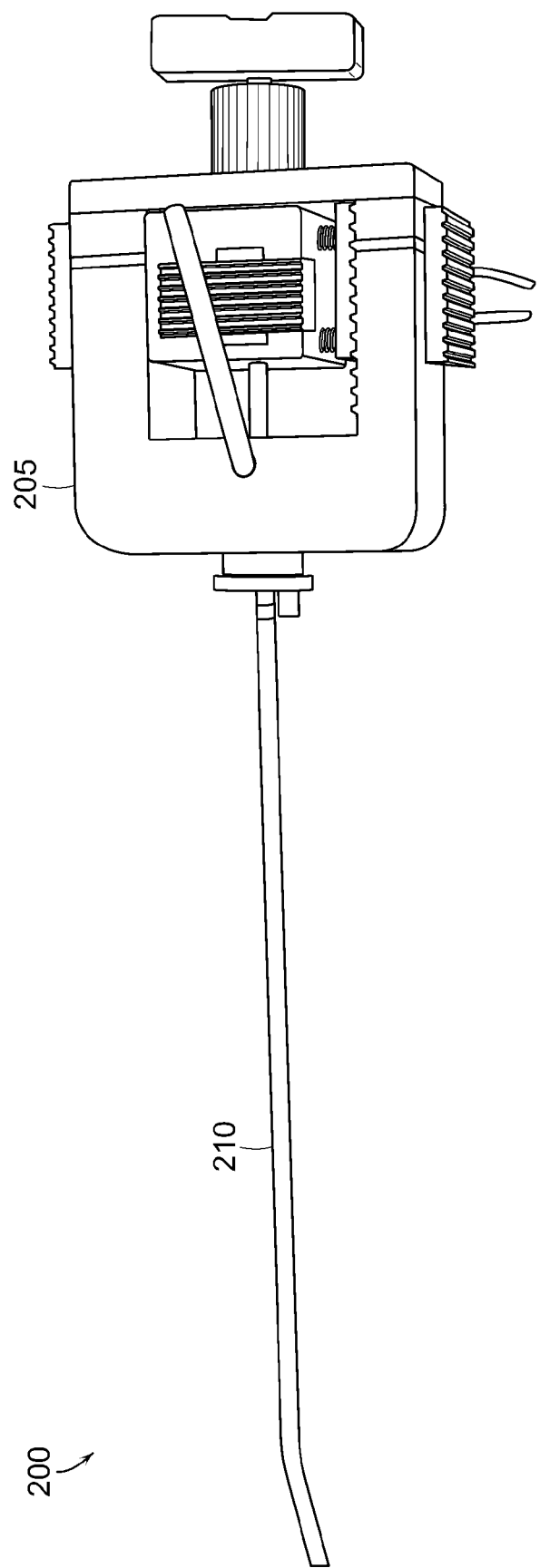
FIG. 3A is a schematic plan view of a delivery system and collapsed stent, in accordance with one embodiment of the invention.
Figure 3B:
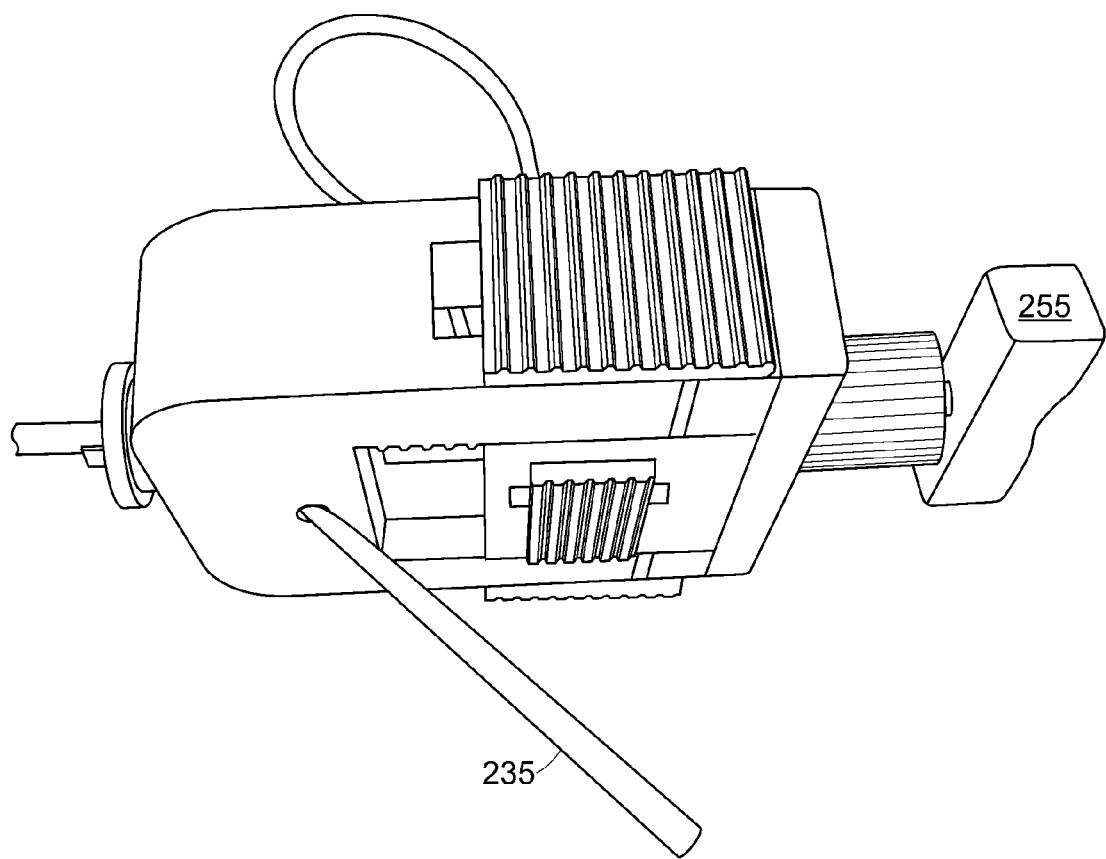
FIG. 3B is a schematic perspective view of the handle of the delivery system of FIG. 3A.
Figure 3C:
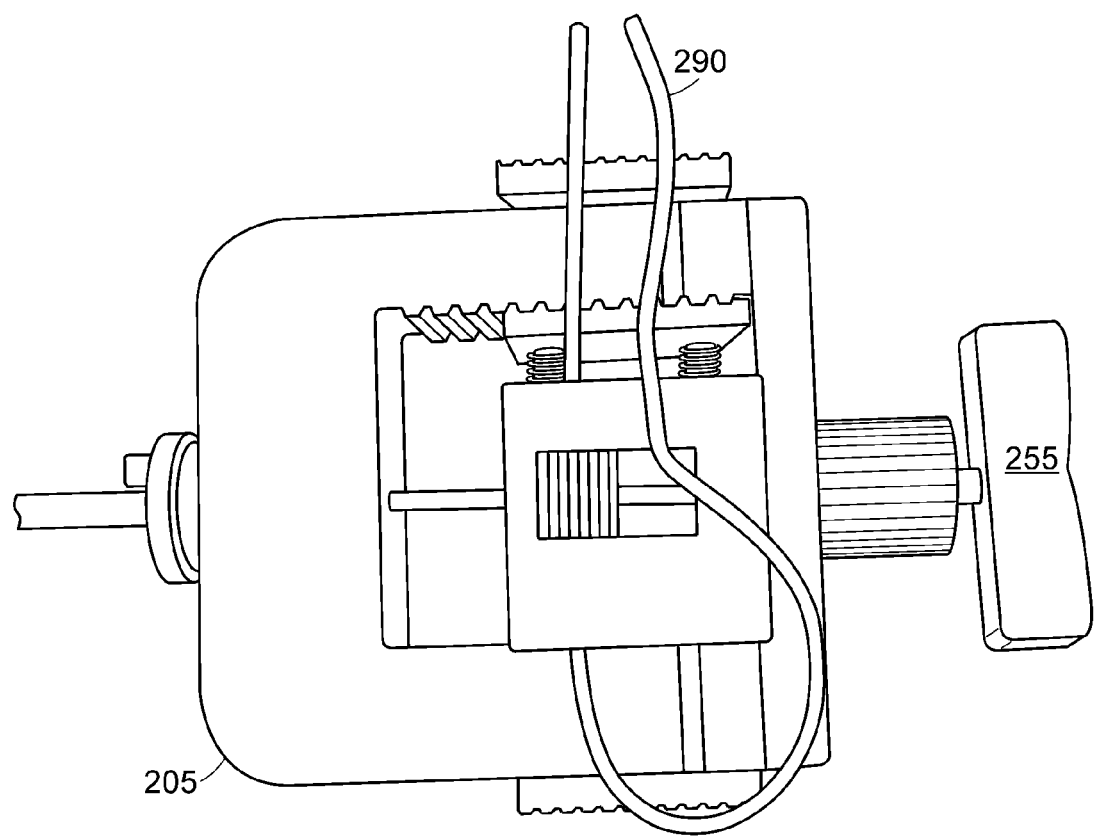
FIG. 3C is a schematic plan view of the handle of the delivery system of FIG. 3A.

One example embodiment may include inserting a delivery system 200 into the cannula such that the covered stent is extended beyond the distal end of the cavity and into the curvilinear cavity. An example of a delivery system prior to insertion into a cannula is shown in FIGS. 3A-3C. Once the delivery system 200 is fully inserted within the cannula, the delivery system 200 can engage with, and be locked in place by, a locking element associated with the cannula. In one embodiment of the invention, the delivery system 200 may be extended through the cannula until a user can feel resistance to the forward movement, indicating that the end of the collapsed stent is abutting against the distal end of the cavity created within the vertebral body. In an alternative embodiment, the length of the cavity may be carefully measured such that the end of the collapsed stent will automatically extend to the end of the cavity upon insertion of the delivery system 200. In addition to these techniques, or in place of these techniques, representative fluoroscopic photos or movies, or use of other appropriate medical imaging techniques, may be taken to ensure the correct placement of the stent within the cavity.

Figure 3D:
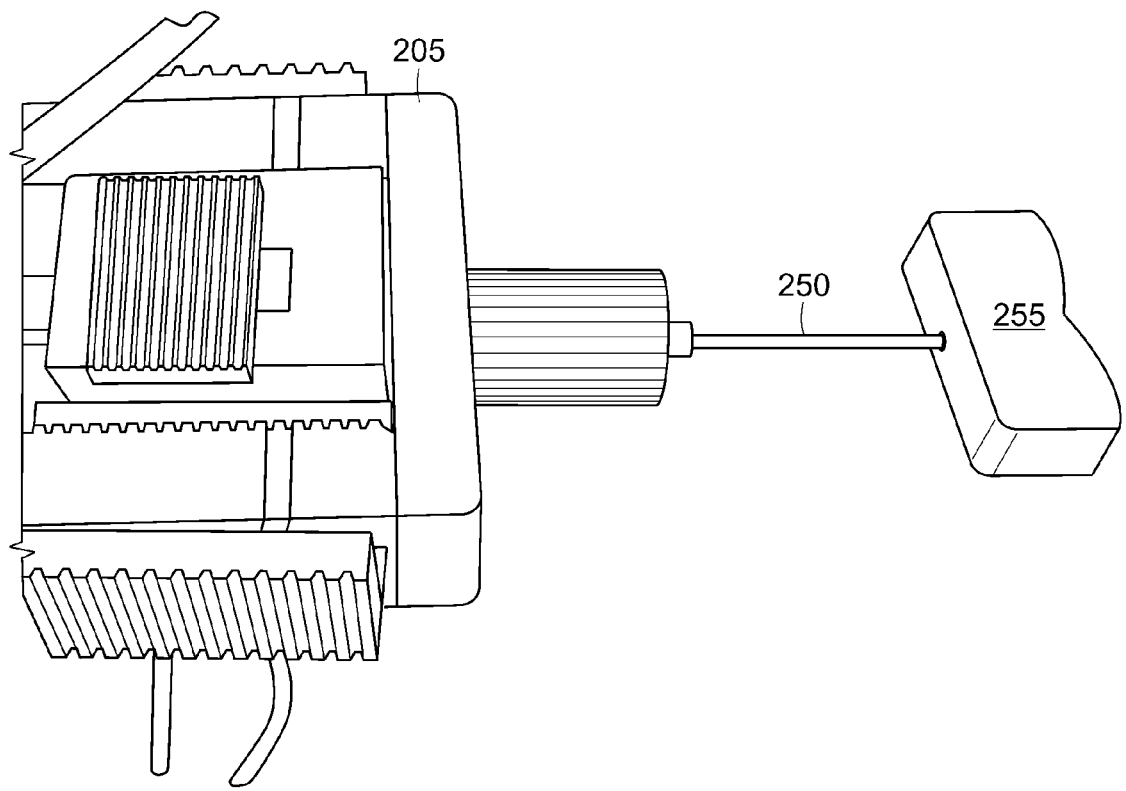
FIG. 3D is a schematic perspective view of the handle of the delivery system of FIG. 3A, with the flexible guidewire (e.g., nitinol wire) retracted.

Once the stent has been correctly positioned within the cavity in its collapsed configuration, it may be expanded within the cavity. In one embodiment, the inner core assembly (i.e., polymer extrusion and guidewire 250) inserted through the center of the delivery system 200 and abutting against the distal end of the stent may be pulled back, for example by pulling on a handle 255 attached to the flexible guidewire 250 and twisting off the bayonet retention feature of the mounting element 260 attached to the polymer extrusion, thus relieving the force on the distal end of the stent that is assisting in maintaining the stent in a collapsed configuration. In one example embodiment, the flexible guidewire 250 and handle 255 may be pulled back by approximately two inches, or by a greater or lesser distance, as required. In an alternative embodiment, the flexible guidewire 250 and handle 255 may be removed completely. In a further alternative embodiment, there is no need for the inner core assembly (i.e., polymer extrusion and guidewire 250) to be inserted within the delivery system 200, with the sheath 230 alone being sufficient to maintain the stent in a fully collapsed configuration. An example of a flexible guidewire 250 and handle 255 being retracted can be seen in FIG. 3D.

Figure 3E:
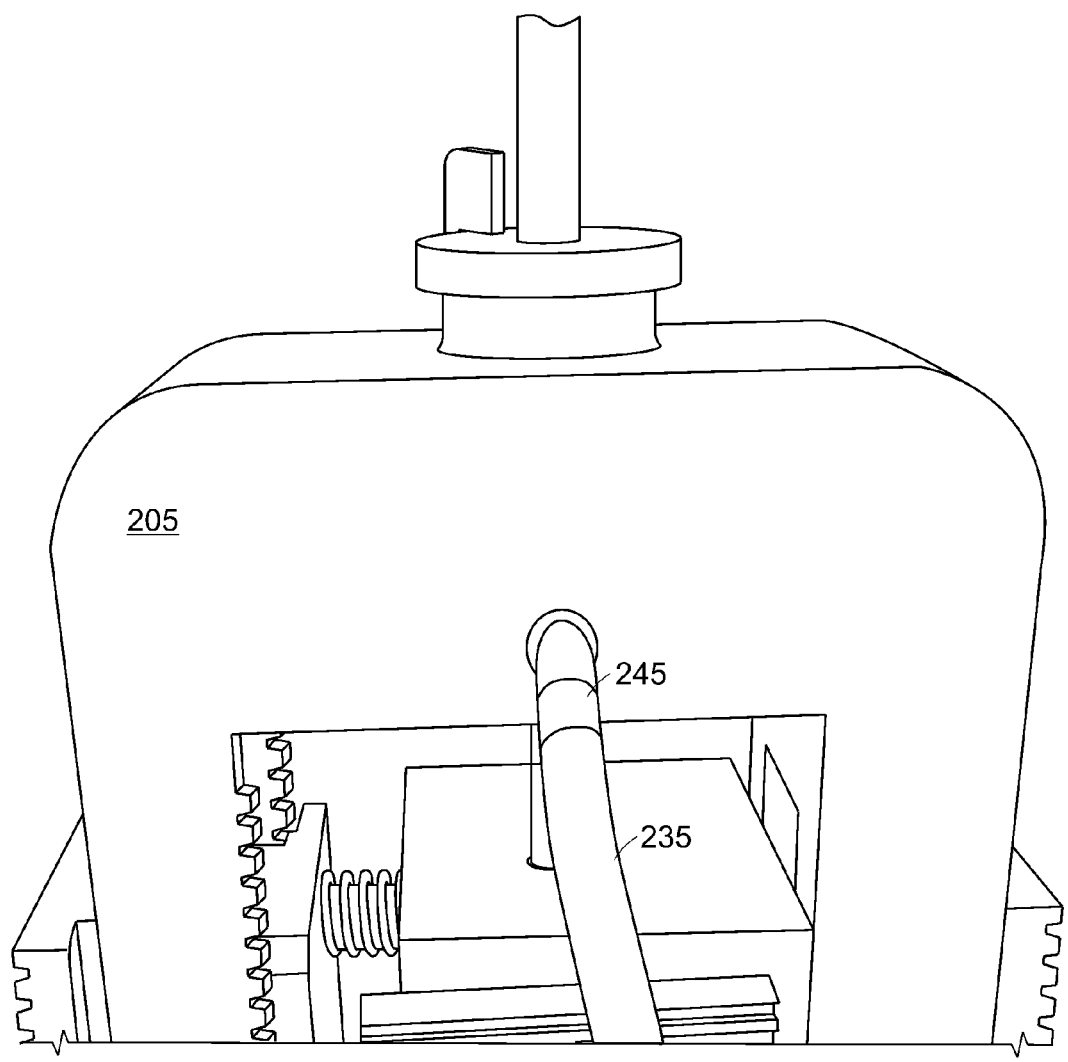
FIG. 3E is a schematic perspective view of the handle of the delivery system of FIG. 3A, with the sheath retracted.
Figure 3F:
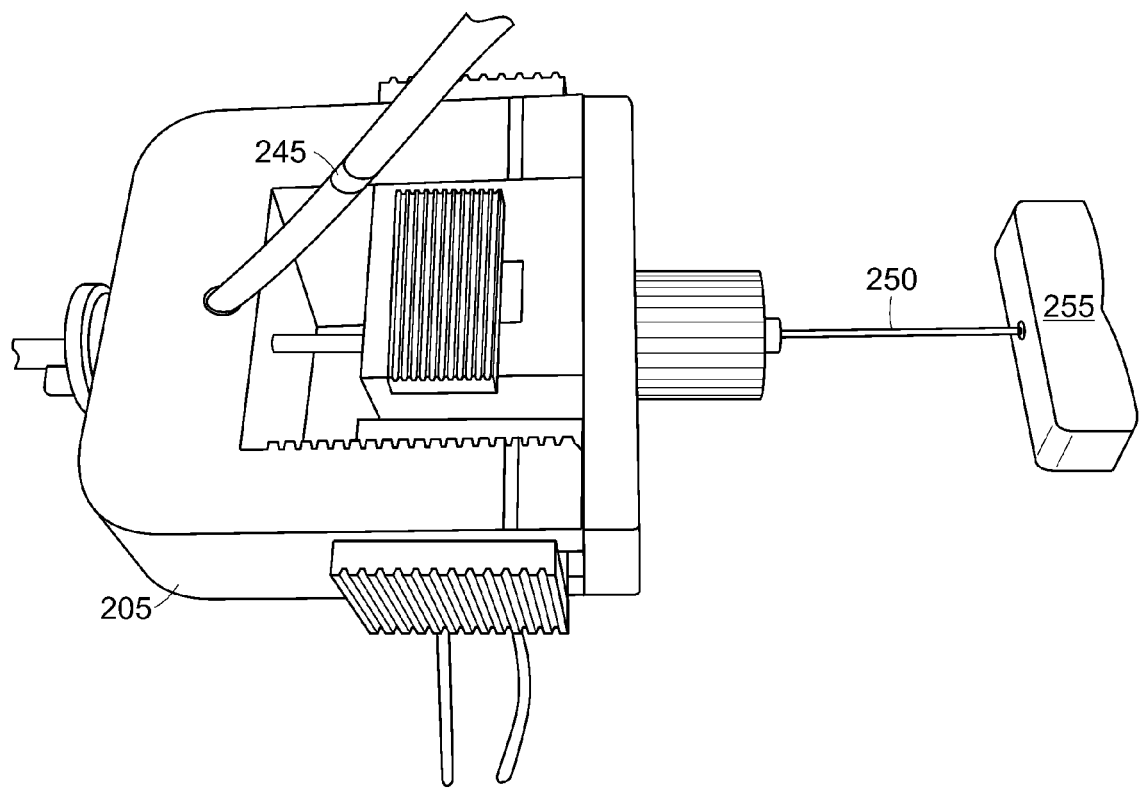
FIG. 3F is a schematic perspective view of the handle of the delivery system of FIG. 3A, with the flexible guidewire (e.g., nitinol wire) and sheath retracted.
Figure 3G:
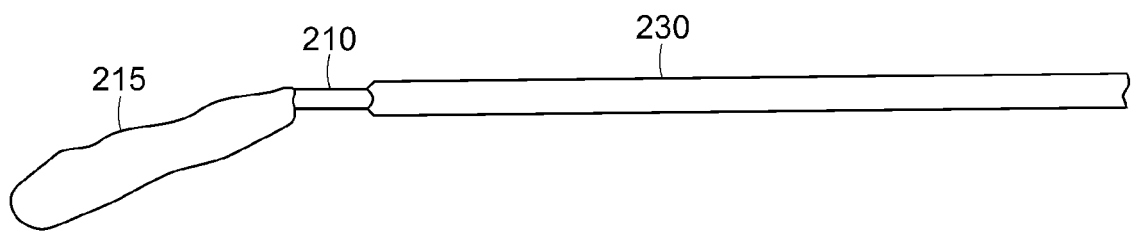
FIG. 3G is a schematic perspective view of a stent coupled to the delivery system of FIG. 3A, with the sheath retracted.

Once the force on the distal end of the stent, provided by the flexible guidewire 250 and/or polymer extrusion, has been removed, the stent is ready to be expanded. Expansion of the stent can be executed by retracting the sheath 230, for example by pulling on a handle attached to the sheath, by a predetermined amount. A mark 245 may be placed on the sheath 230 to indicate when the sheath 230 has been pulled back by the correct amount. Retracting the sheath 230 removes the external restrictive force on the stent and allows it to self-expend to its preformed, free-state configuration. This may, in one embodiment of the invention, substantially conform to the size and shape of the cavity. An example of a sheath 230 after being retracted can be seen in FIGS. 3E and 3F. In an alternative embodiment, the sheath 230 can be removed prior to the polymer extrusion being removed. An example of a stent 215 with the sheath 230 retracted but with the polymer extrusion remaining in place and extended to the distal end of the stent 215 can be seen in FIG. 3G.

Figure 3H:
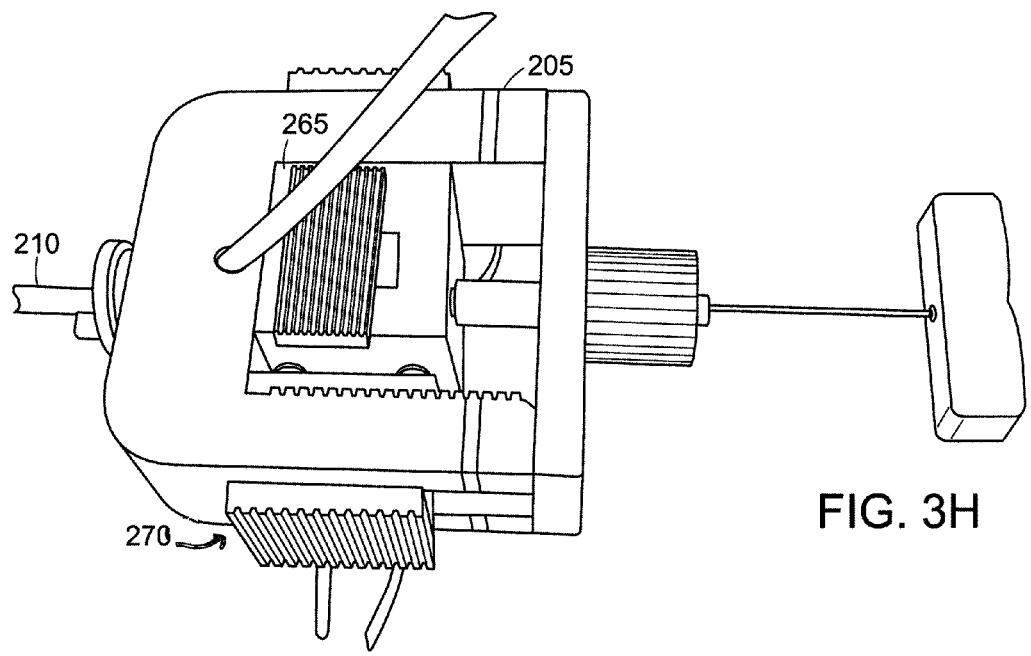
FIG. 3H is a schematic perspective view of the handle of the delivery system of FIG. 3A, with the sliding mechanism extended forward.

In one embodiment of the invention, expansion of the stent 215 can also result in a certain amount of foreshortening at the distal end of the stent 215. This foreshortening, which is caused by the increase in the diameter of the stent 215 as it expands resulting in a responsive decrease in the length of the stent 215, may retract the end of the stent 215 slightly from the distal end of the cavity. This may be compensated for by providing a force to push the entire stent 215 forward until the distal end of the expanded stent 215 abuts against the distal end of the cavity. This may be achieved through the use of a sliding mechanism 265 that is configured to allow for the extension and retraction of the entire stent 215 and elongated shaft 210 arrangement along the axis of the shaft. By releasing the locking mechanism 270 on this sliding mechanism 265, the stent 215 and elongated shaft 210 can be pushed forward by the required amount. The sliding mechanism 265 can then re-engage the locking mechanism to lock the stent at a final position. An example of the sliding mechanism 265 pushed forward within the handle 205 can be seen in FIG. 3H.

Figure 3I:
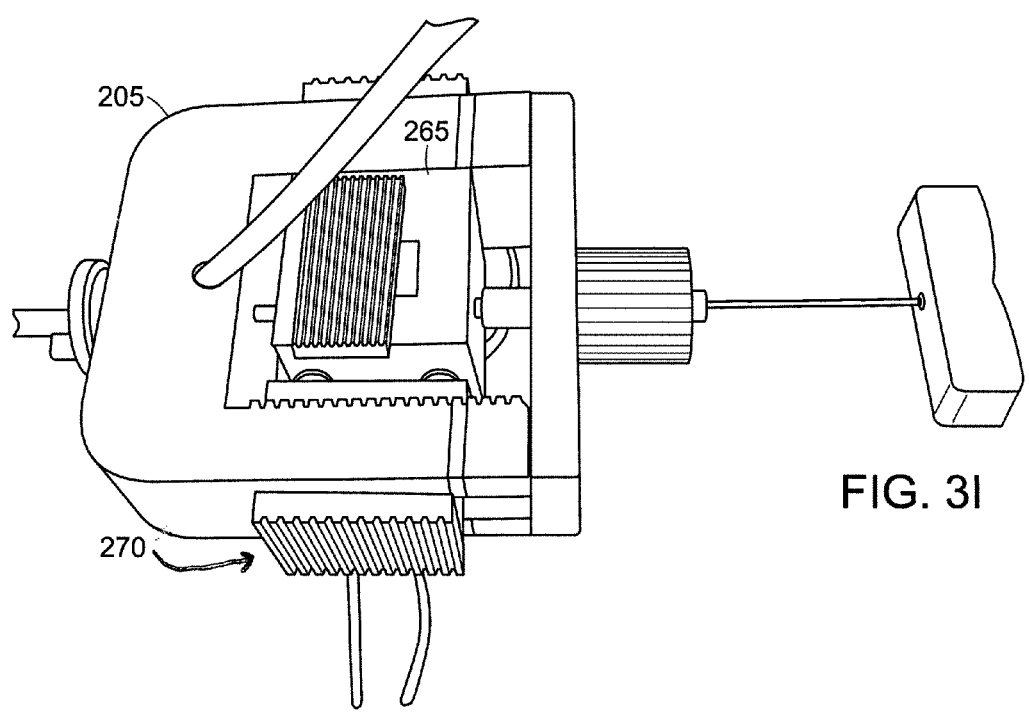
FIG. 3I is a schematic perspective view of the handle of the delivery system of FIG. 3A, with the sliding mechanism retracted to an intermediate position.
Figure 3J:
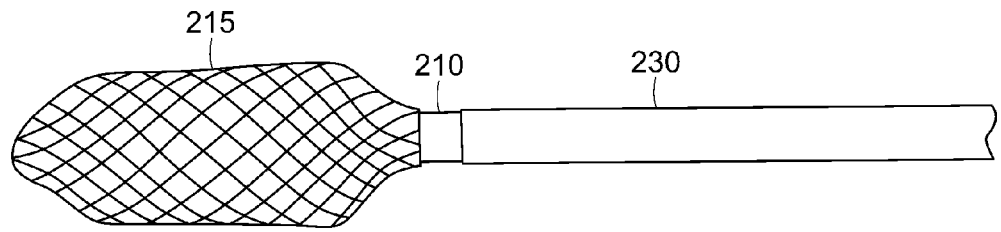
FIG. 3J is a schematic perspective view of an expanded stent coupled to the delivery system of FIG. 3A.

In one embodiment, forcing the expanded stent 215 forward may result a certain amount of foreshortening of the stent 215 at its proximal end (i.e. the end attached to the elongated shaft 210 of the delivery system 200). Here, after forcing the stent 215 forward using the sliding mechanism 265, the sliding mechanism 265 may be retracted by a small amount to counteract any foreshortening at the proximal end of the stent 215. Again, the sliding mechanism 265 may be locked into position once the stent 215 has been correctly positioned. As before, fluoroscopic images, or other appropriate medical images, may be taken to confirm the positioning and expansion of the stent at the distal end of the cavity. In one embodiment of the invention, the polymer extrusion may also be used to extend the expanded stent after foreshortening due to the expansion. An example of the sliding mechanism 265 retracted after being pushed forward within the handle 205 can be seen in FIG. 3I. An example of a fully expanded stent 215 coupled to a hollow elongated shaft 210 with a sheath 230 retracted can be seen in FIG. 3J.

As mentioned above, the polymer extrusion can perform the function of collapsing the stent by stretching the stent out longitudinally or axially, by applying a force in that direction from within the stent. The proximal end of the stent is fixed to the elongate shaft 210 and the distal end of the stent is stretched and held in place by the polymer extrusion which is locked in position to the handle 205 by the mounting element 260. With the stent collapsed, it can be moved easily down the working channel, thereby eliminating the need for a sheath in the delivery system.

Figure 3K:
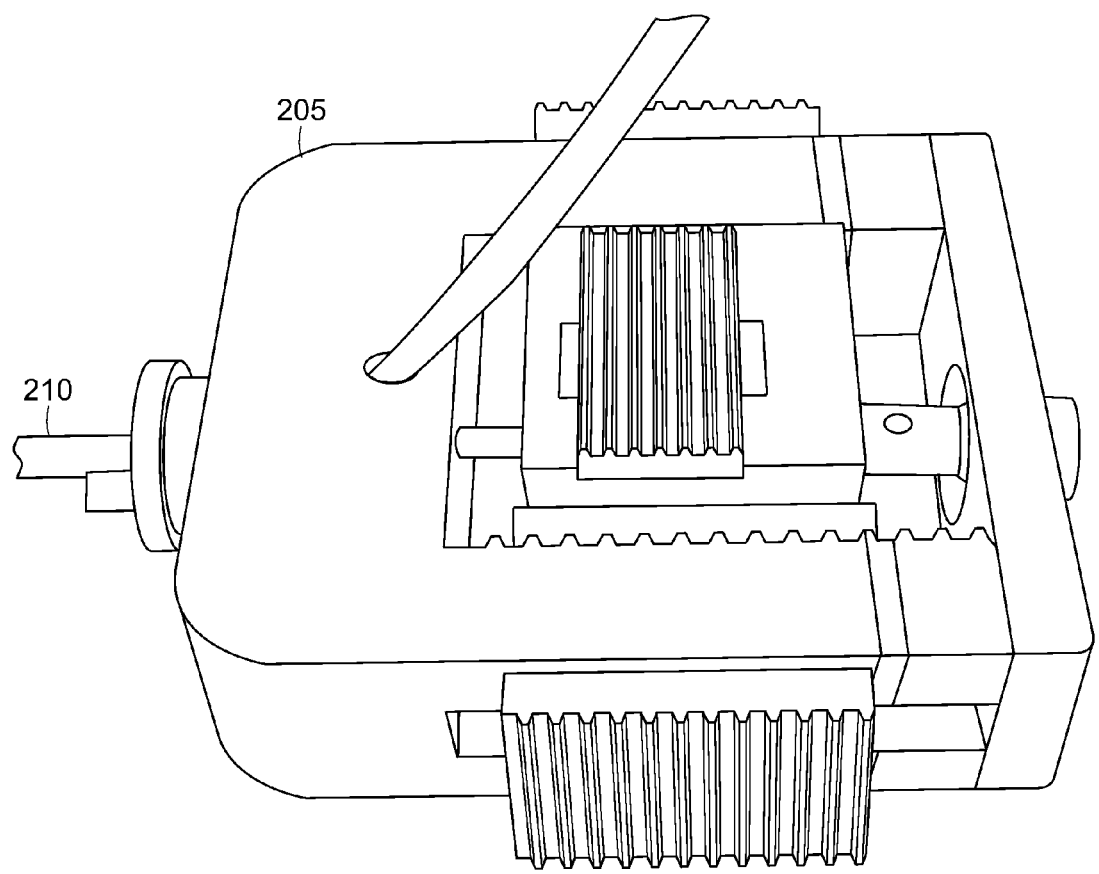
FIG. 3K is a schematic perspective view of the handle of the delivery system of FIG. 3A, with the inner core assembly (i.e., polymer extrusion and flexible guidewire) removed.

After correct positioning of the expanded stent 215, the polymer extrusion can be removed completely from the delivery system 200 by releasing and retracting the mounting element 260 from the handle portion 205. Removing the polymer extrusion leaves a hollow shaft 210 through the center of the delivery system 200 and into the interior of the expanded stent 215. This hollow shaft can then be used for the injection of cement, or other material, into the stent. An example of the delivery system with the polymer extrusion removed can be seen in FIG. 3K.

Figure 3L:
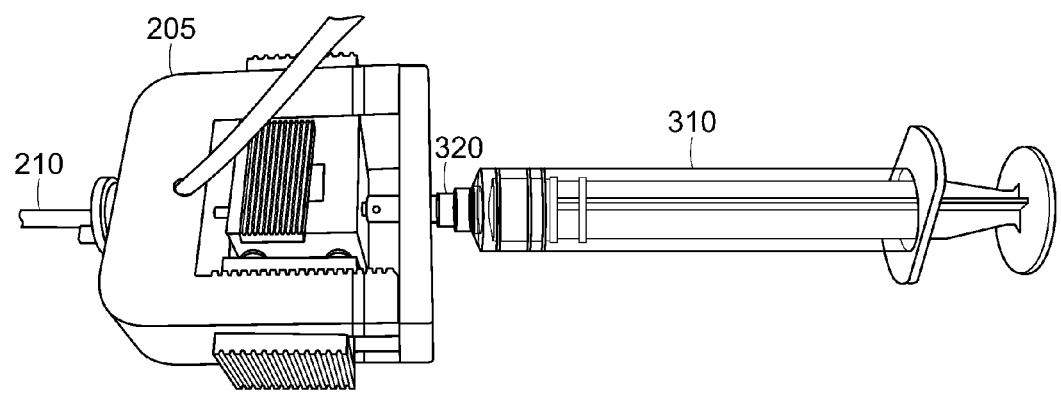
FIG. 3L is a schematic perspective view of the handle of the delivery system of FIG. 3A, with a syringe attached.

Injection of cement into the stent may be performed by releasably connecting the end of a syringe 310 to the hollow shaft at the point vacated by the polymer extrusion mounting element 260. In one embodiment of the invention, a 10 cc threaded syringe may be used, although in alternative embodiments, any appropriate injection device may be utilized. In one embodiment, the proximal end of the hollow shaft may include a luer lock 320, or other releasable locking arrangement, that may engage the end of the syringe 310 and engage it with the hollow shaft 210. An example of a syringe 310 attached to the handle 205 of the delivery system 200 can be seen in FIG. 3L. Alternatively, instead of directly rigidly connecting the syringe 310 to the handle 205, a rigid or flexible extension tube can be interdisposed between the syringe 310 and the handle 205. The extension tube allows the physician to have his hands out of the fluoroscopic field and also provides the opportunity to reorient the syringe 310, e.g., by forming an "elbow" or other angular connection, so that the syringe 310 is not fixedly cantilevered axially from the delivery system 200.

Once the syringe 310 is in place, the cement, or other material, such as a cement analogue, can be injected into the hollow shaft 210 of the delivery system 200 and into the expanded stent 215. Injection of cement may be continued until the stent 215 is completely filled and cement flows out of the designated holes in the stent into the vertebral body. Once enough cement has flowed out of the stent 215 and into the vertebral body to provide the required level of interdigitation between the stent 215 and vertebral body, the injection can be stopped. Again, fluoroscopic images, or other appropriate medical images, may be taken to confirm that the stent has been filled and the required amount of cement has flowed out into the vertebral body at the correct positions.

Figure 3M:
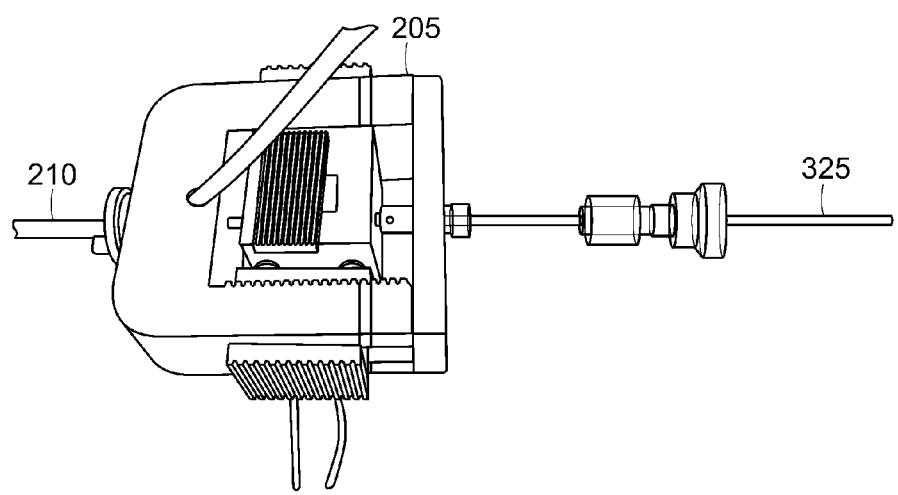
FIG. 3M is a schematic perspective view of the handle of the delivery system of FIG. 3A, with the cement piston inserted to push through additional cement.
Figure 3N:
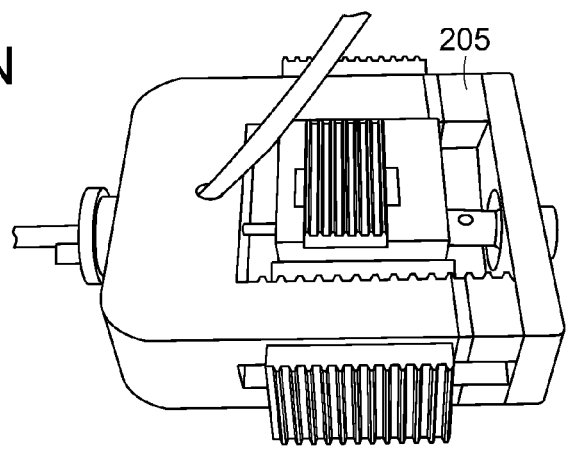
FIG. 3N is a schematic perspective view of the handle of the delivery system of FIG. 3A, with the cement piston removed.

In one embodiment of the invention a cement piston 325 may be used to push additional cement in the hollow shaft 210 into the stent 215, for example when high cement viscosity has resulted in incomplete filling of the cavity. This may be achieved by simply detaching the syringe 310, and pushing the cement piston 325 back into the hollow shaft 210 to force the additional cement in the shaft 210 into the stent 215. This may be important if the physician is not satisfied with the amount of cement filling prior to removal. In one embodiment, the hollow shaft 210 can hold 1.5 cc of cement, or other material, with the cement piston 325 capable of pushing any percentage of that volume into the stent 215, as required. Once the correct amount of cement has been injected into the stent 215, the cement piston 325 can again be removed. An example of the cement piston 325 forcing cement through the shaft 210 can be seen in FIG. 3M. An example of the handle 205 of the delivery system 200, after the cement piston 325 has been removed again, can be seen in FIG. 3N.

Figure 3O:
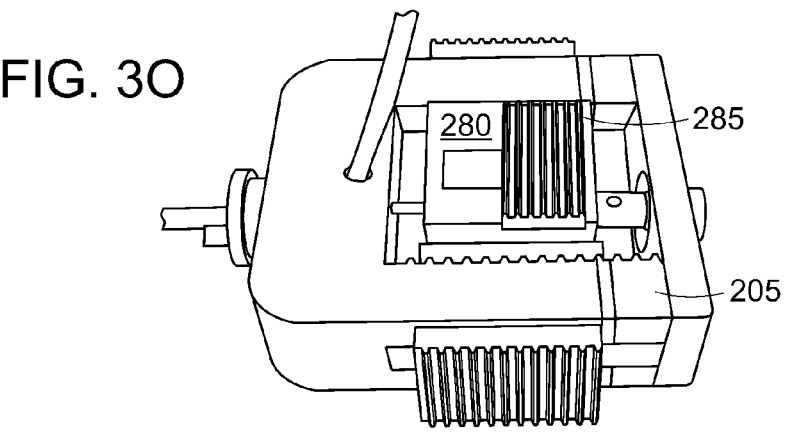
FIG. 3O is a schematic perspective view of the handle of the delivery system of FIG. 3A, with the locking mechanism unlocked.
Figure 3P:
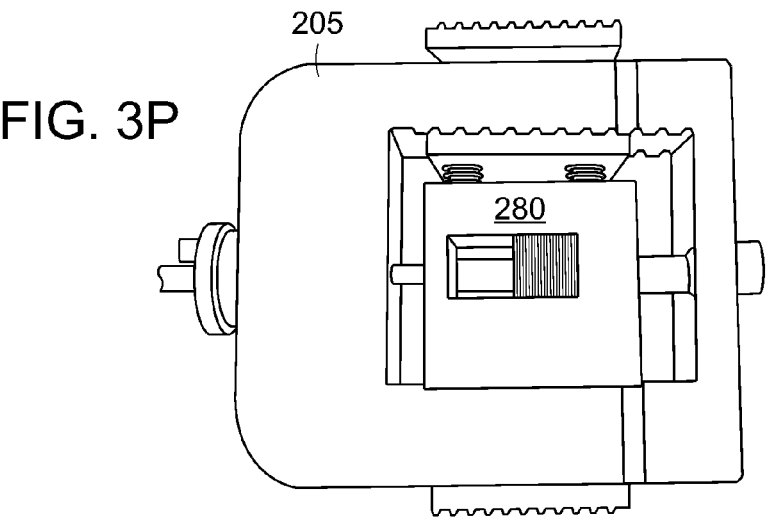
FIG. 3P is a schematic perspective view of the rear of the handle of the delivery system of FIG. 3A, with the locking mechanism unlocked.

After the stent 215 has been filled with cement, and the correct amount of cement has exited the stent 215 through the exit holes to interdigitate with the vertebral body, the stent 215 can be released from the delivery system 200 and the delivery system 200 removed. In one embodiment of the invention, a locking mechanism 280 may be used to hold the stent 215 onto the delivery system 200. This locking mechanism 280 may include any appropriate means of releasably engaging the proximal end of the stent, including, but not limited to, a clamping mechanism, a grasping mechanism, sliding mechanism, a pressure fit between an outer shaft, the proximal end of the stent, and the inner hollow shaft, or any other appropriate mechanism. In one embodiment, the locking element 285 may include a slide, switch, or other element at the proximal end of the delivery system, allowing the locking mechanism to disengage from the stent when required. A removable pin 290, or other locking device, may be inserted into the delivery system 200 to ensure that the delivery system 200 is not disengaged from the stent 215 inadvertently, before the cement has been fully injected. An example of the locking mechanism 280 after the pin 290 has been removed and the locking mechanism 280 opened is shown in FIGS. 3O and 3P.

Once the stent has been released from the delivery system, the delivery system can be unlocked and removed from the cannula. After this, the cannula may be removed and the surgical incision closed.

In an alternative embodiment, a delivery system including a handle adapted to move multiple components of the delivery system with a movement of a single user control mechanism can be used to deploy a stent within a cavity created within a vertebral body. This user control mechanism can include a mechanism such as, but not limited to, a rotating mechanism, a sliding mechanism, a trigger mechanism, or any other appropriate mechanical, electrical, and/or magnetic mechanism.

Employing a user control mechanism to control a number of functions of the delivery system can both simplify and speed up the deployment process, while reducing the number of steps that need to be performed by a user during the deployment process. This can increase the efficiency of the delivery system while increasing the safety of the deployment methods for a patient being treated. In one embodiment, a user control mechanism can control the retraction of a sheath covering the stent, the movement of an inner shaft, and/or the movement of an outer shaft. The inner shaft can include, but is not limited to, a flexible guidewire, a hollow flexible shaft, and/or another appropriate elongate element configured to extend through the interior of an outer shaft. The outer shaft can include, but is not limited to, a hollow elongate shaft configured to releasably engage the stent at its distal end.

In an alternative embodiment, additional and/or different functions of the delivery system can be controlled by a single user control mechanism. These functions can include, but are not limited to, injecting filler material such as cement into the stent, releasing the stent, locking, and/or unlocking, the delivery system to/from the cannula, curving the distal end of the flexible shaft to facilitate deployment of the stent within a curved cavity, and/or any other appropriate function of a stent delivery system.

In one embodiment, a user control mechanism is adapted to retract the outer sheath of the elongate shaft of a delivery system to allow the stent to be fully deployed within a cavity in a vertebral body. At the same time, the inner and outer shafts of the elongate shaft are moved forward to compensate for any foreshortening of the stent during retraction of the sheath, as described above. This allows the stent to be deployed in its expanded configuration at the full distal extent of the cavity. The user control mechanism can be configured to move the sheath and the inner and outer shafts simultaneously in opposite directions by set amounts, with the sheath being retracted towards the handle of the delivery system while the inner and outer shafts are extended outwards away from the handle.

The distance by which each of the sheath and the inner and outer shaft should be moved relative to each other is dependent upon factors that can include the size and shape of the stent and the cavity in which the stent is being deployed. For example, in one embodiment, the sheath can be retracted by a distance equal to or greater than the length of the stent to ensure that it is fully retracted from the stent in order to allow the stent to expand fully. The inner and outer shafts, in contrast, can be extended by a distance equal to the foreshortening of the stent as it expands from its collapsed configuration to its expanded configuration. In one embodiment, the inner and outer shafts can be extended out from the handle by the same distance. In an alternative embodiment, the inner shaft and the outer shaft can be extended out from the handle by different distances.

Example user control mechanisms for moving multiple components of a delivery system can be seen in FIGS. 4A-8B.

Figure 4A:
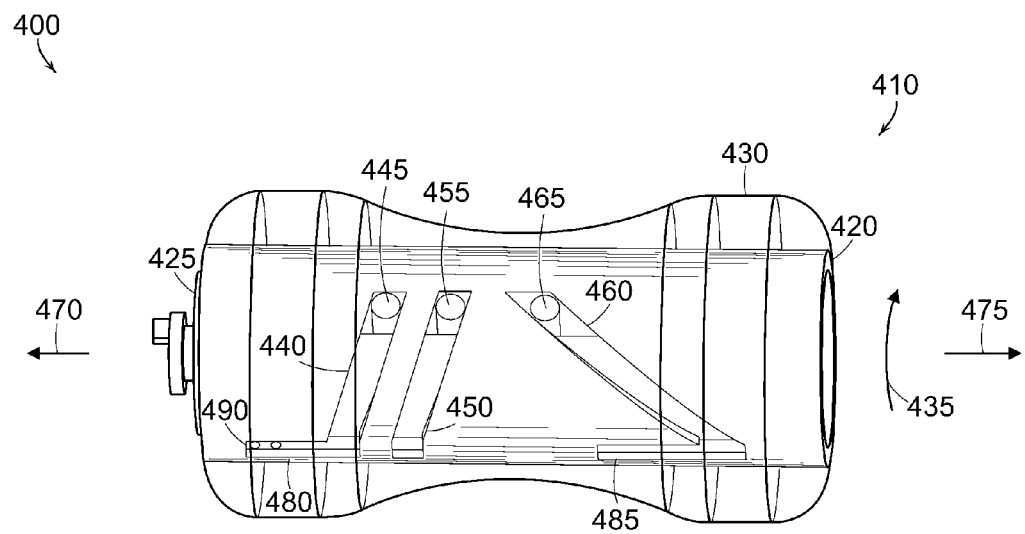
FIG. 4A is a schematic side view of a handle for a delivery system with a rotational cam mechanism, in accordance with one embodiment of the invention.
Figure 4B:
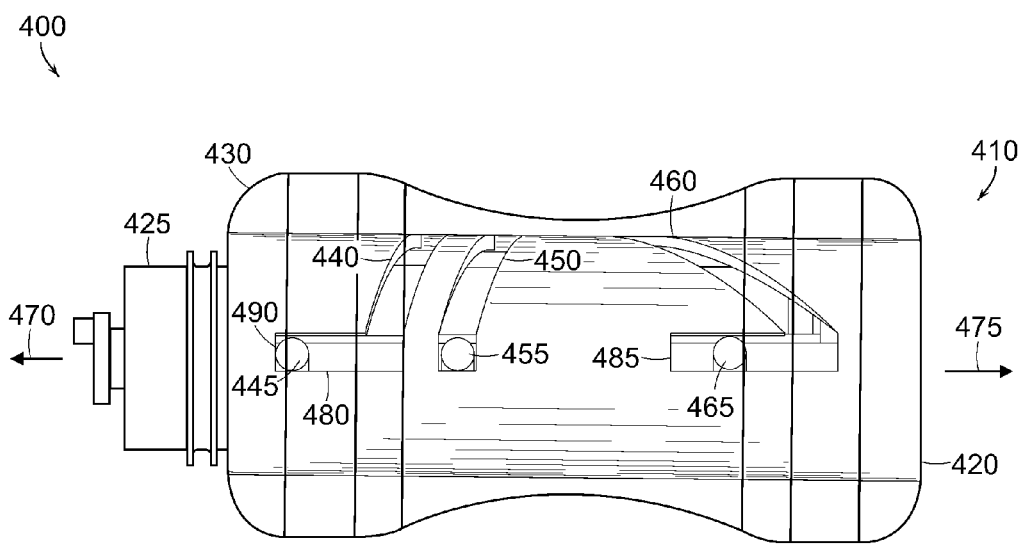
FIG. 4B is a schematic side view of the handle of FIG. 4A after being turned.
Figure 4C:
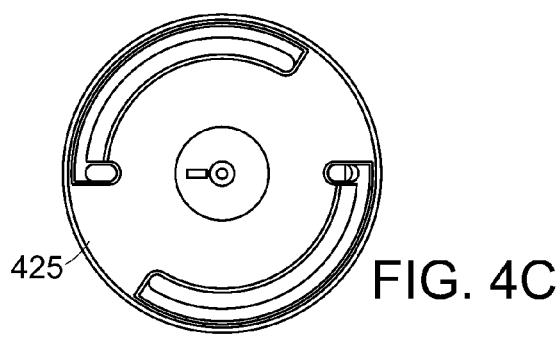
FIG. 4C is a schematic end view of another handle for a delivery system with a rotational cam mechanism, in accordance with one embodiment of the invention.
Figure 4D:
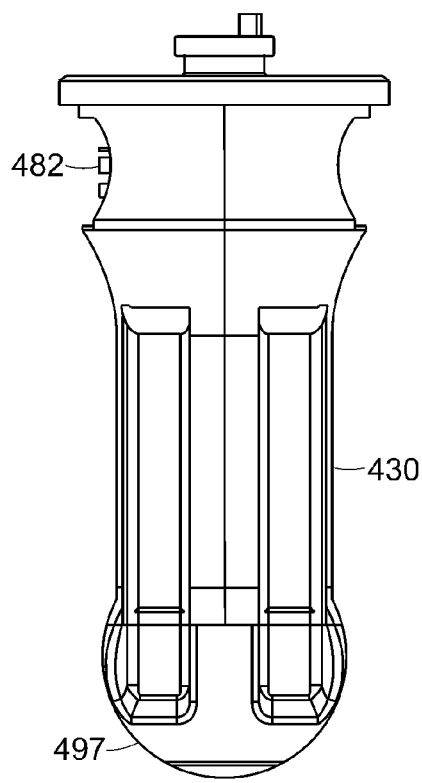
FIG. 4D is a schematic side view of the handle of FIG. 4C.
Figure 4E:
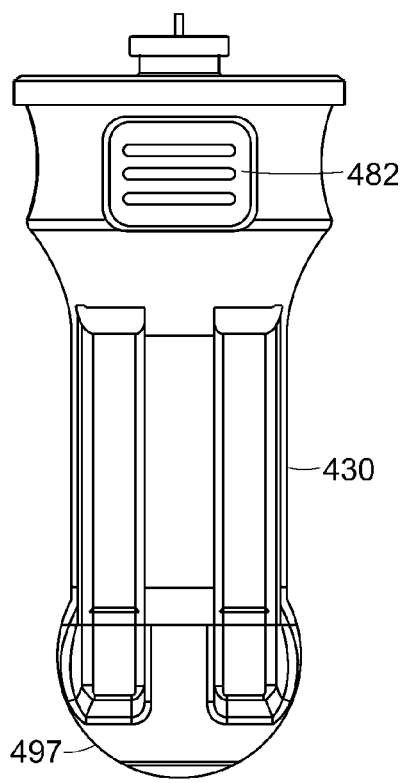
FIG. 4E is a schematic plan view of the handle of FIG. 4C.
Figure 4F:
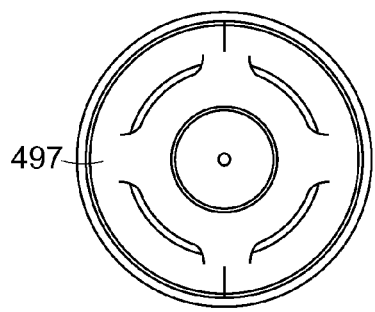
FIG. 4F is another schematic end view of the handle of FIG. 4C.

FIGS. 4A and 4B show a handle 400 for a delivery system with a rotational cam mechanism 410 before and after being rotated. The rotational cam mechanism 410 includes three separate slotted cam shafts wrapped helically on a support element 420 surrounding the central shaft 425 of the handle 400. An outer grip 430 covers the support element 420 and central shaft 425 and engages with the support element 420. Pins associated with each of the outer shaft, the inner shaft, and the sheath engage with the slotted cam shafts such that a rotation 435 of the support element 420 will force the pins axially along the central shaft of the delivery device in a direction and distance controlled by the angle and direction of each slotted cam shaft.

More specifically, a first slotted cam shaft 440 engages with a first pin 445 attached to the outer shaft of a delivery system. A second slotted cam shaft 450 engages with a second pin 455 attached to the inner shaft of the delivery system. And, a third slotted cam shaft 460 engages with a third pin 465 attached to a sheath (not shown). As a result, as the outer grip 430 is rotated about the central shaft 425 of the handle 400, the first pin 445 and second pin 455 will be forced axially forward 470 toward the distal end of the handle 400, resulting in the inner shaft and outer shaft being extended outwards from the distal end of the handle 400 (and therefore compensating for any forshortening of the stent during deployment). Simultaneously, the third pin 465 will be pulled axially rearwards 475 toward the proximal end of the handle 400, resulting in the sheath being pulled rearwards 475 towards the handle (and therefore exposing the stent).

In one embodiment, the helical paths for each of the inner shaft and outer shaft have the same angle, resulting in the distal ends of the inner shaft and outer shaft each being forced forward 470 the same distance. In an alternative embodiment, the helix paths for each of the inner shaft and outer shaft may be different, resulting in the distal ends of the inner shaft and outer shaft being forced forward 470 by a different amount. In a further alternative embodiment, at least one of the inner shaft and outer shaft may be stationary.

Additional axially slotted cam shafts can be located at the distal end of the first slotted cam shaft 440 and third slotted cam shaft 460, allowing the first pin 445 and third pin 465 to remain in the same axial position while the second pin 455 is moved rearwards 475 by pulling the outer grip 430 rearwards 475 towards the proximal end of the handle 400 of the delivery system after the rotation of the outer grip is completed. By having axial slots of different lengths, the pins can be moved axially by different distances when the outer grip is pulled rearwards 475 towards the proximal end of the handle. For example, the first axial slotted cam shaft 480 (associated with the outer shaft) is shorter than the second axial slotted cam shaft 485 (associated with the sheath), so that when the outer grip 430 is pulled rearwards 475, the second pin 455 is moved rearwards 475 along with the outer grip 430, the first pin 445 remains stationary until it connects with the end 490 of the first axial slotted cam shaft 480, after which it moves rearwards 475 along with the outer grip 430, and the third pin 465 remains stationary throughout the entire axial rearward 475 motion of the outer grip 430. In alternative embodiments, different lengths of axial cam shafts can be associated with any of the pins, allowing for different rearward travel distances, as desired. By moving the outer shaft back a certain distance after being pushed forward, while leaving the inner shaft extended, the stent can be stretched out and fully deployed without the distal end of the stent being pulled back from the distal end of the cavity. In an alternative embodiment, there are no axial cam shafts.

In one example embodiment, the outer grip 430 can be rotated through approximately 120° to fully move the sheath, inner shaft, and outer shaft (and thus deploy the stent). In an alternative embodiment, a larger or smaller rotation of the outer grip 430, for example between 90° and 360°, can be used.

Another example of a handle 400 for a delivery system with a rotational cam mechanism 410 is shown in FIGS. 4C-4J. In this embodiment, the delivery system includes a handle portion 400 and a hollow elongate shaft (not shown) extending from the distal end of the handle 400. The hollow elongate shaft can include a distal end adapted to support and deploy a stent within a cavity created within a vertebral body. The hollow elongate shaft can include an inner shaft and an outer shaft adapted to engage a stent, releasably positioned at the distal end of the elongate shaft. A sheath can be positioned over the outer shaft and extend over the stent to maintain the stent in a collapsed configuration during insertion through the cannula and into the cavity.

Figure 4G:
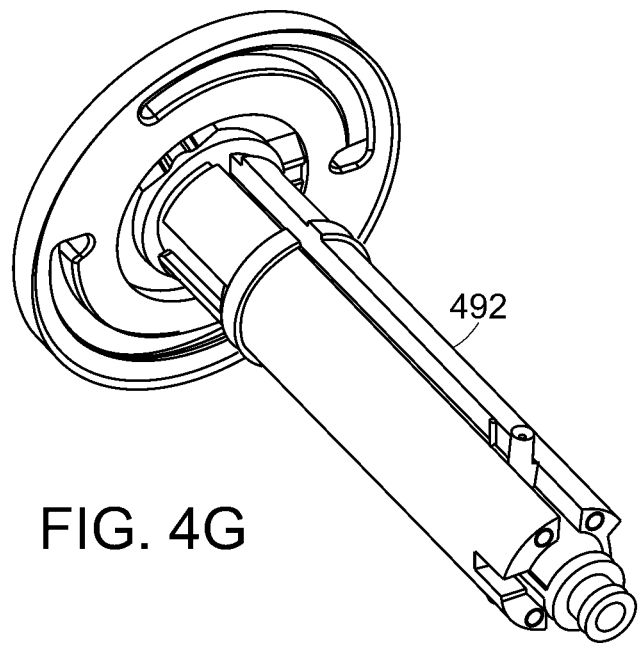
FIG. 4G is a schematic perspective view of a linear sleeve for the handle of FIG. 4C.
Figure 4H:
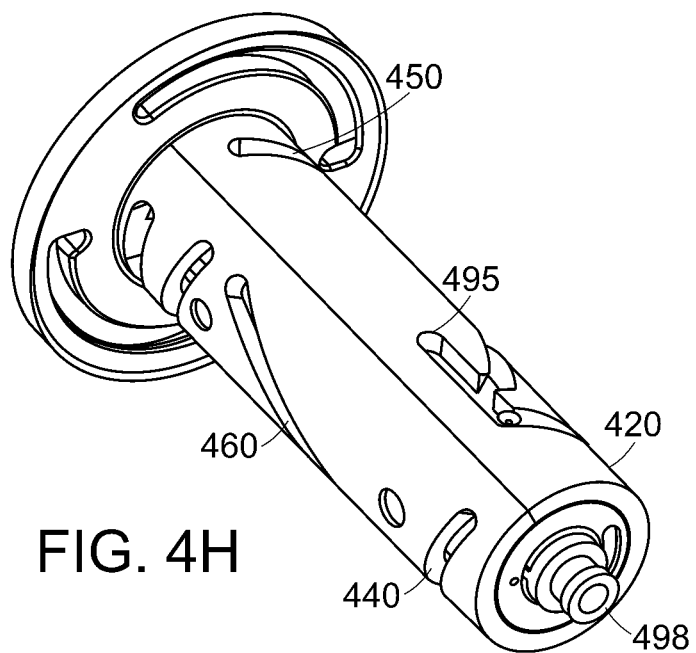
FIG. 4H is a schematic perspective view of a support element on a linear sleeve for the handle of FIG. 4C.
Figure 4I:
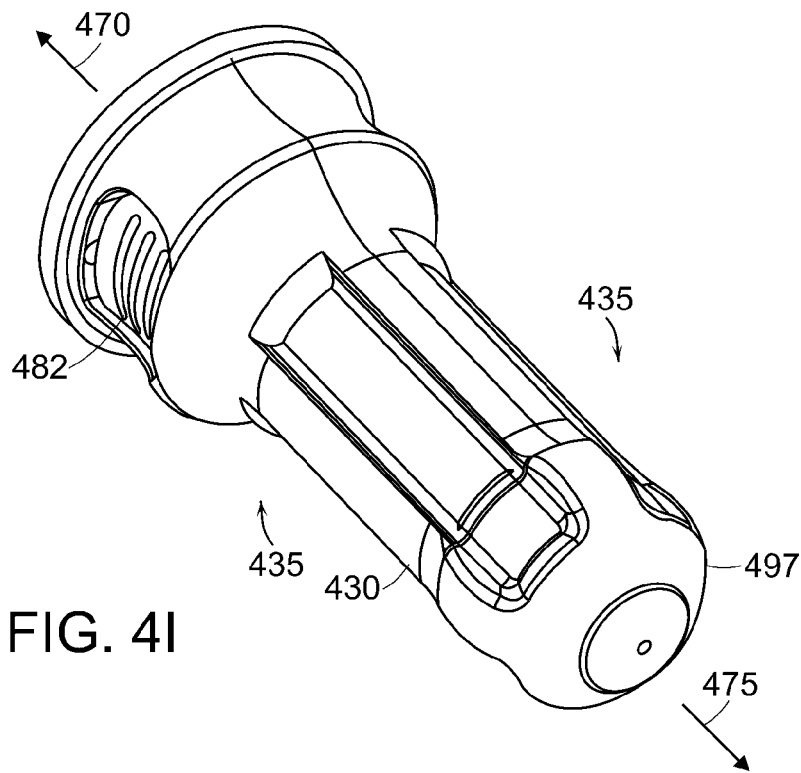
FIG. 4I is a schematic perspective view of the handle of FIG. 4C.
Figure 4J:
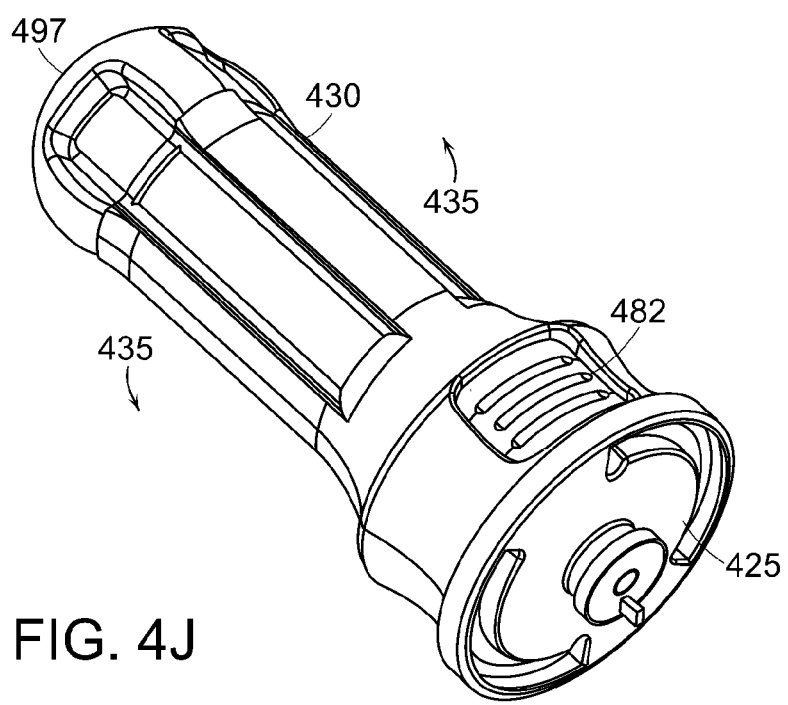
FIG. 4J is another schematic perspective view of the handle of FIG. 4C.

As with the embodiment of FIGS. 4A and 4B, the rotational cam mechanism 410 includes three separate slotted cam shafts wrapped helically on a support element 420 surrounding the central shaft 425 of the handle 400. An outer grip 430 covers the support element 420 and central shaft 425 and engages with the support element 420. Pins 445, 455, 465 (associated with each of the outer shaft, the inner shaft, and the sheath) engage with the slotted cam shafts 440, 450, 460 such that a rotation 435 of the support element 420 will force the pins 445, 455, 465 axially along the central shaft of the delivery device in a direct and distance controlled by the angle and direction of each slotted cam shaft 440, 450, 460. In one embodiment, the pins 445, 455, 465 are positioned within a linear support sleeve 492 that is configured to ensure that the pins 445, 455, 465 can only move axially, either forwards 470 or backwards 475, along the length of the handle 400. A schematic perspective view of the linear support sleeve 492 engaging one of the pins is shown in FIG. 4G, with FIG. 4H showing the support element 420 positioned on the linear support sleeve 492.

A single axial slotted cam shaft 495 is located at the distal end of the first slotted cam shaft 440 and third slotted cam shaft 460, allowing the first pin 445 and third pin 465 to moved rearwards 475 together. A removable cap 497 is placed on the proximal end of the handle 400 to cover a luer lock 498 adapted for engagement with a filler material delivery device, such a syringe.

A stent release button 482 is located on the handle 400 to actuate disengagement of the stent from the elongate shaft once deployment and filling of the stent is completed. The stent release button 482 can be depressed and slid rearwards 475 towards the proximal end of the handle 400 (i.e. away from the elongate shaft) to release the stent from the elongate shaft. In an alternative embodiment, two stent release buttons located opposite each other on either side of the handle 400 can be used. In a further alternative embodiment, any appropriate user interface elements including, but not limited to, a dial, a switch, a sliding element, or a button, can be used to activate the detachment of the stent from the elongate shaft, and/or to perform any other required functions.

Figure 5:
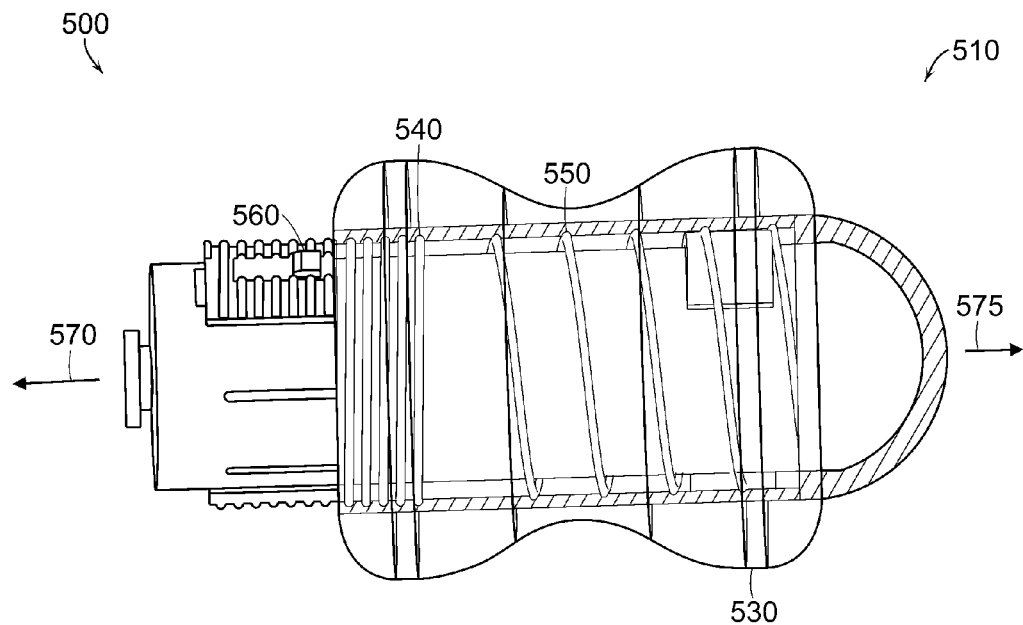
FIG. 5 is a schematic side view of a handle for a delivery system with a rotational threaded mechanism, in accordance with one embodiment of the invention.

FIG. 5 shows a handle 500 for a delivery system with a rotational threaded mechanism 510. The rotational cam mechanism 510 includes two separate threads wrapped helically on a support element 520 surrounding the central shaft 525 of the handle 500. An outer grip 530 covers the support element 520 and central shaft 525 and engages with the threads on the support element 520. A first thread 540 is associated with the sheath of the delivery system, while a second thread 550 is associated with at least one of the inner shaft and outer shaft of the delivery system. A slotted control button 560 can provide a user control for additional functions of the delivery system.

In operation, a rotation of the outer grip 530 will drive the sheath (associated with the first thread 540) in an axially rearward 575 direction, while the inner and/or outer shaft (associated with the second thread 550) will be driven in an axially forward 570 direction. The helical angle of each thread will determine how far each element is moved axially through the rotation of the outer grip 530. In an alternative embodiment, larger or smaller helical angles can be used to move one or more elements by any required distance, as appropriate. In addition, more threads, at any required helical angle, can be incorporated into the rotational threaded mechanism 510 to control additional elements of the delivery system.

In an alternative embodiment, a geared mechanism can be used to control the movement of the inner shaft, the outer shaft, the sheath, and/or any other appropriate element of the delivery system. The geared mechanism can include a number of gear arrangements, including any appropriately configured and sized gears to move the shafts and/or sheath in different directions and by different distances, as required sequentially or simultaneously. An example geared mechanism 610 can be seen in FIG. 6.

Figure 6:
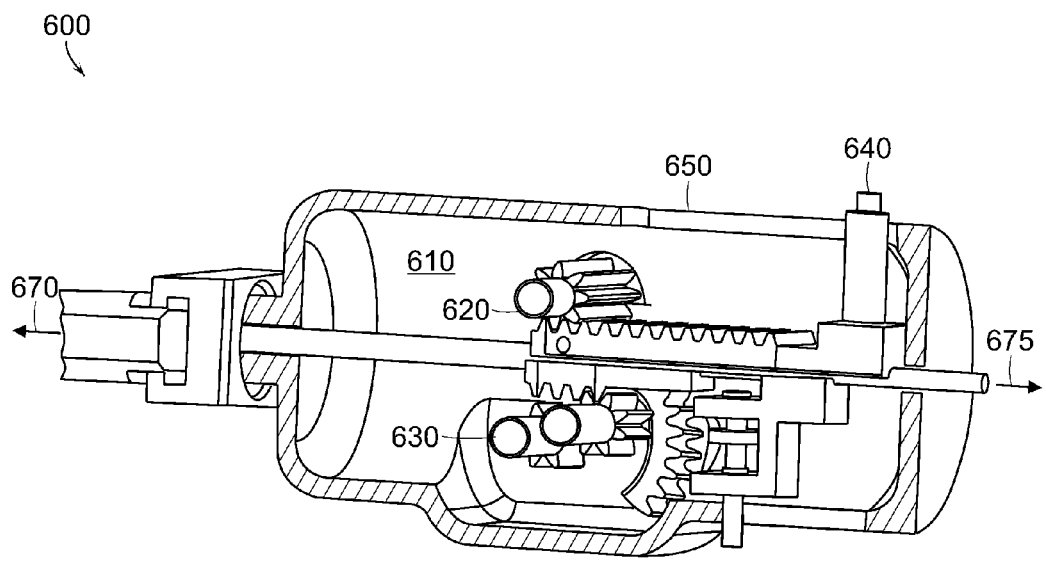
FIG. 6 is a schematic side view of a handle for a delivery system with a geared mechanism, in accordance with one embodiment of the invention.

FIG. 6 shows a handle 600 for a delivery system with a geared mechanism 610. The geared mechanism 610 includes a first gear arrangement 620, engaging the sheath, and a second gear arrangement 630 for controlling the movement of one of more of the inner and outer shafts. In operation, a pin 640 can be moved in a rearward direction 675 by a user, thus pulling the sheath rearwards 475 by a distance corresponding to the length of the slot 650. The first gear arrangement 620 will be driven by the movement of the pin 640, which will in turn drive the second gear arrangement 630 and push the inner shaft and/or outer shaft in a forward direction 670. Through careful selection of the slot 650 and gearing arrangements 620, 630, the sheath and the inner and/or outer shafts can be moved by any appropriate distance and in either the forward 670 or rearward 675 direction. Different gearing arrangements to drive additional and/or different elements can be used, as appropriate. In an alternative embodiment, a dial associated with a gearing element, or other appropriate user control, can be used instead of, or in addition to, the pin.

Figure 7:
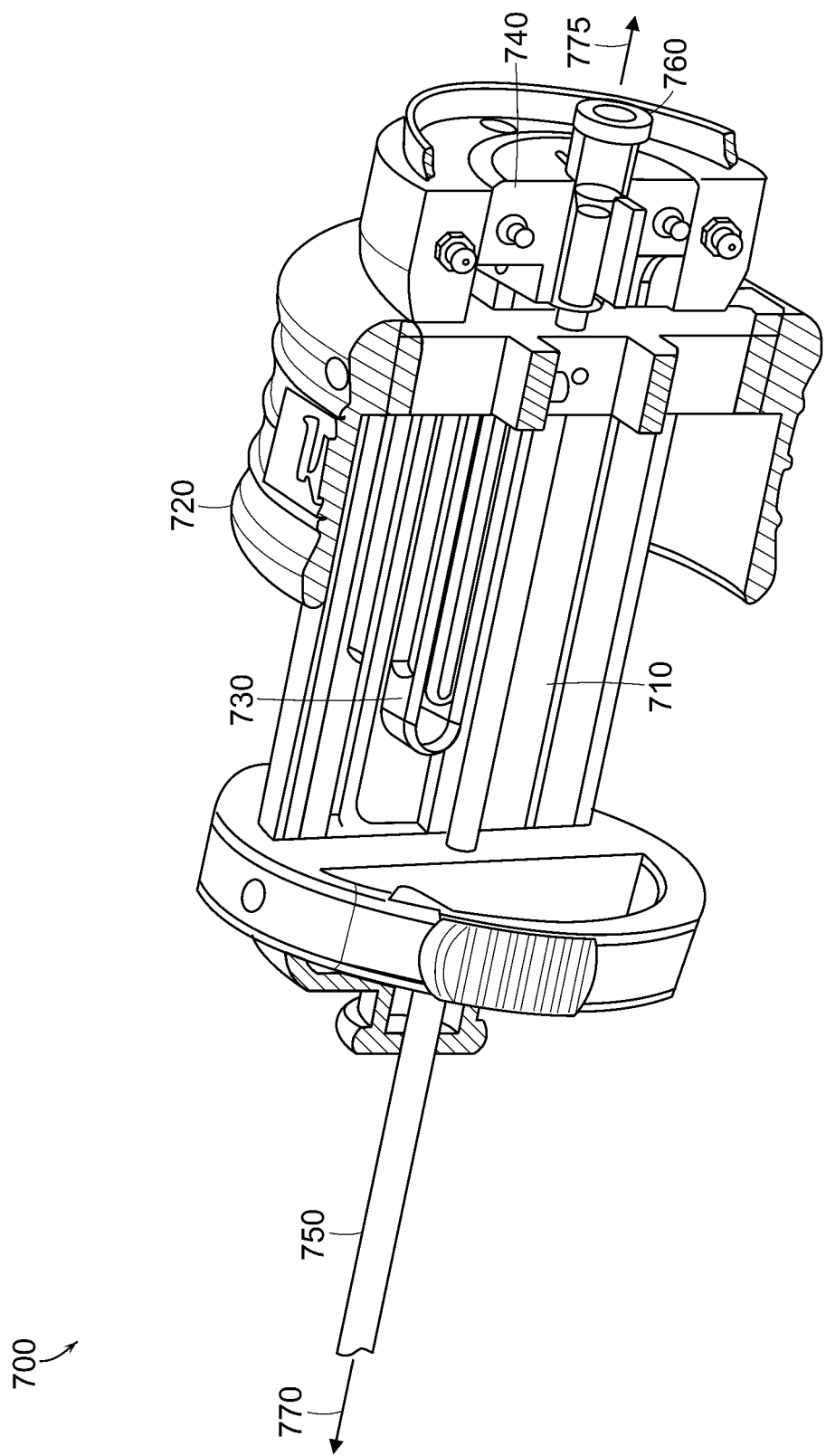
FIG. 7 is a schematic side view of a handle for a delivery system with a sliding belt mechanism, in accordance with one embodiment of the invention.

FIG. 7 shows a handle 700 for a delivery system with a sliding belt mechanism 710. The sliding belt mechanism 710 includes a sliding outer grip 720 that is coupled to an inner sliding belt arrangement 730 that forces an inner element 740 in a forward 770 direction as the sliding outer grip 720 is pushed in a rearward 775 direction by a user.

More specifically, the sheath is attached to the sliding outer grip 720, while the inner shaft and outer shaft are connected to the inner element 740. By coupling the sheath, inner shaft, and/or outer shaft of the elongate shaft 750 to either the sliding outer grip 720 or the inner element 740, each shaft and sheath can be moved forwards 770 or rearwards 775, as required. The sliding belt mechanism can provide simultaneous movement of the shafts and/or sheath, but may also provide sequence in the movement of the shafts and/or sheath by delaying one function through the belt arrangement 730. As before, a luer lock 760 can be placed at a proximal end of the handle 700 to provide a coupling element for a cement deliver device, such as a syringe.

Figure 8A:
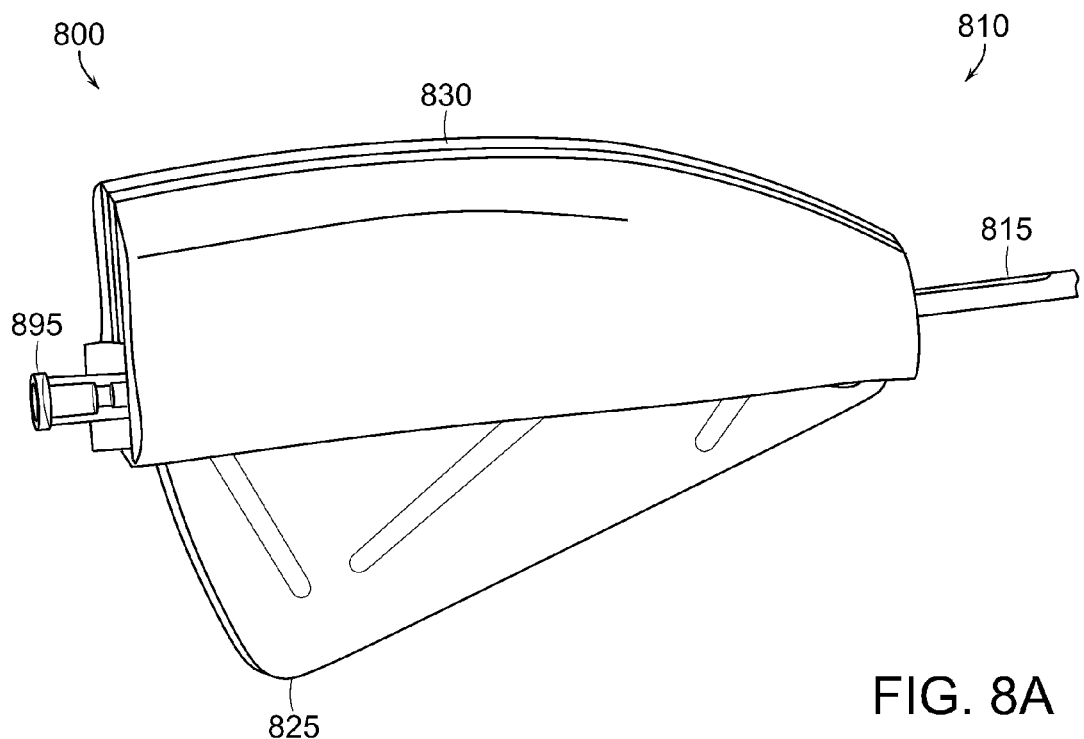
FIG. 8A is a schematic perspective view of a handle for a delivery system with a triggering mechanism, in accordance with one embodiment of the invention.
Figure 8B:
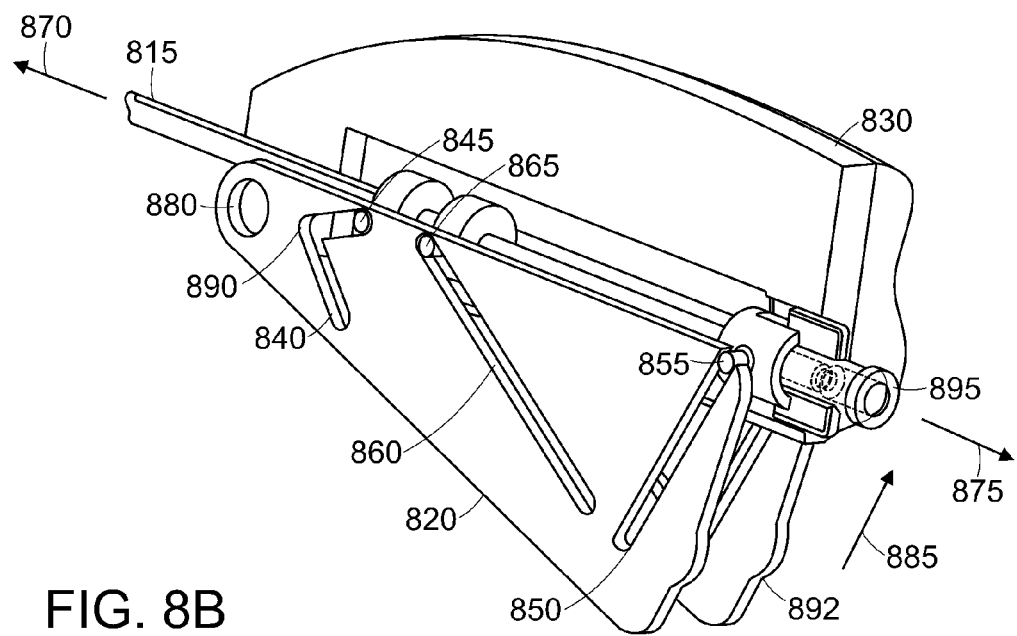
FIG. 8B is a schematic perspective view of the interior cam mechanism of the handle of FIG. 8A.

FIGS. 8A and 8B show a handle 800 for a delivery system with a triggering mechanism 810. The triggering mechanism 810 includes three separate slotted cam shafts positioned on a pair of cam plates 820 within a trigger 825 that is pivotably connected to a support element 830. Pins associated with each of the outer shaft, the inner shaft, and the sheath of the elongate shaft 815 engage with the slotted cam shafts such that a closing of the trigger 825 will force the pins axially along the central shaft 835 of the delivery device in a direct and distance controlled by the angle and direction of each slotted cam shaft. This configuration can result in a simple mechanical delivery system that is easy to use.

More specifically, a first slotted cam shaft 840 engages with a first pin 845 attached to the outer shaft of a delivery system. A second slotted cam shaft 850 engages with a second pin 855 attached to the inner shaft of the delivery system. And, a third slotted cam shaft 860 engages with a third pin 865 attached to a sheath. As a result, as the trigger 825 is closed by being pivoted 885 into the support element 830 about a pivot point 880, the first pin 845 and second pin 855 will be forced axially forward 870 toward the distal end of the handle 800, resulting in the inner shaft and outer shaft being extended outwards from the distal end of the handle 800 (and therefore compensating for any foreshortening of the stent during deployment). Simultaneously, the third pin 865 will be pulled axially rearwards 875 toward the proximal end of the handle 800, resulting in the sheath being pulled rearwards 875 towards the handle 800 (and therefore exposing the stent).

The first slotted cam shaft 840 includes a bend 890, resulting in the first pin 845 (and therefore the outer shaft) being moved forward 870 initially before being moved in a rearward direction 875 during a second portion of the closing motion. In alternative embodiments, any one or more of the cam shafts can be curved, bent, and/or angled in any appropriate manner to produce the required forwards and/or rearward movement of each element of the delivery system. In a further alternative embodiment, none of the cam shafts include a bend.

As before, a luer lock 895 can be placed at a proximal end of the handle 800 to provide a coupling element for a cement delivery device, such as a syringe. In one embodiment, a bump 892 on a rear portion of one or both of the cam plates 820 can engage and force the release of an end cap on the handle 800, thus exposing the luer lock 895 and prompting the user to begin the next stem of the process. In an alternative embodiment, no bump is required, and the end cap of the handle 800 is instead removed manually.

Figure 9:
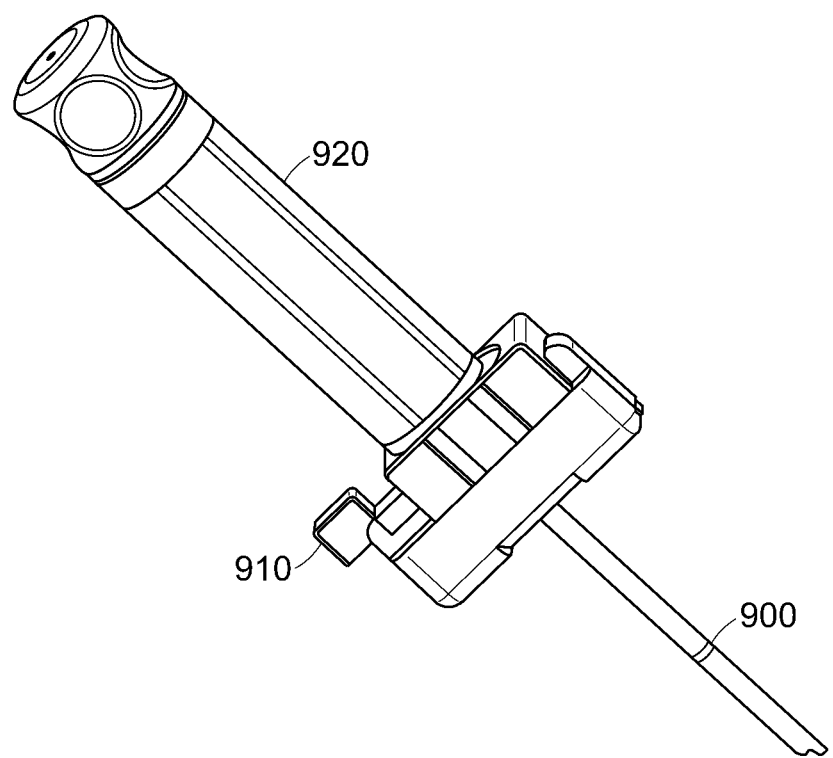
FIG. 9 is a schematic perspective view of a delivery system inserted in a cannula, in accordance with one embodiment of the invention.

In one embodiment, the delivery system may include a locking mechanism adapted to releasably lock the delivery system within a cannula in a required circumferential orientation, to ensure the correct positioning of the stent within the cavity created within the vertebral body. In one embodiment, a spring loaded locking mechanism on the cannula may engage a portion of the handle of the delivery system to releasably lock it in place, with one or more buttons, switches, knobs, or other appropriate user elements, either on the cannula or on the handle of the delivery system, releasing the locking mechanism when the delivery system is to be removed. In one embodiment, the cannula can include a sliding element adapted to engage a protruding flange at a distal end of a handle of a delivery system to releasably lock the delivery device into the cannula. An example cannula 900 including a sliding element 910 for releasably engaging a protruding flange of a delivery system 920 can be seen in FIG. 9. In further embodiments, any other appropriate means of releasably locking the delivery system to the cannula in a required circumferential configuration can be used.

In one embodiment, a key may be positioned on the hollow elongate shaft to mate with a slot in the cannula to ensure that the delivery system is inserted into the cannula in the desired orientation. In an alternative embodiment, at least a portion of the distal end of the handle of the delivery system can be configured to mate with a portion of the cannula, thus ensuring the positioning of the delivery system in the correct orientation.

In one embodiment, as described above, the delivery system can be used to deploy a stent within a cavity created within a vertebral body, wherein the handle is adapted to control multiple components of the delivery system with a movement of a single user control mechanism, such as a rotation, sliding, or triggering of a user control mechanism.

Figure 10A:
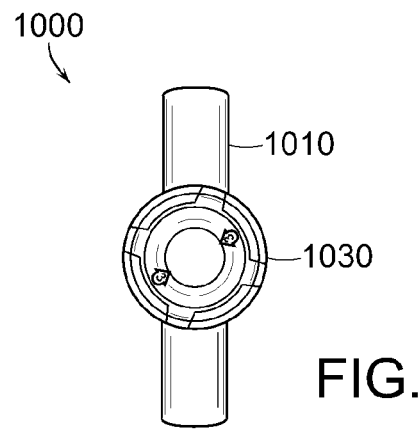
FIG. 10A is a schematic end view of a handle for another delivery system, in accordance with one embodiment of the invention.
Figure 10B:
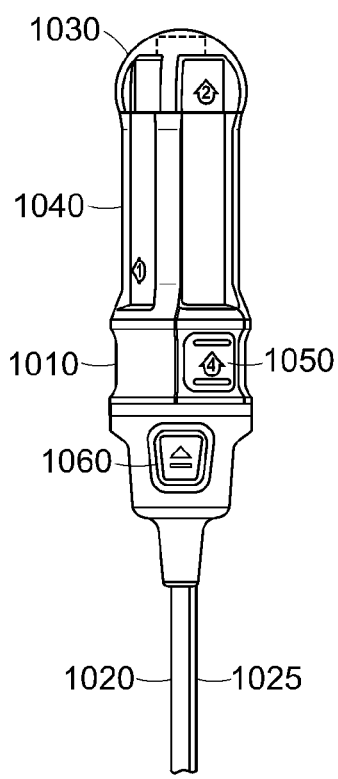
FIG. 10B is a schematic side view of the handle of FIG. 10A.
Figure 10C:
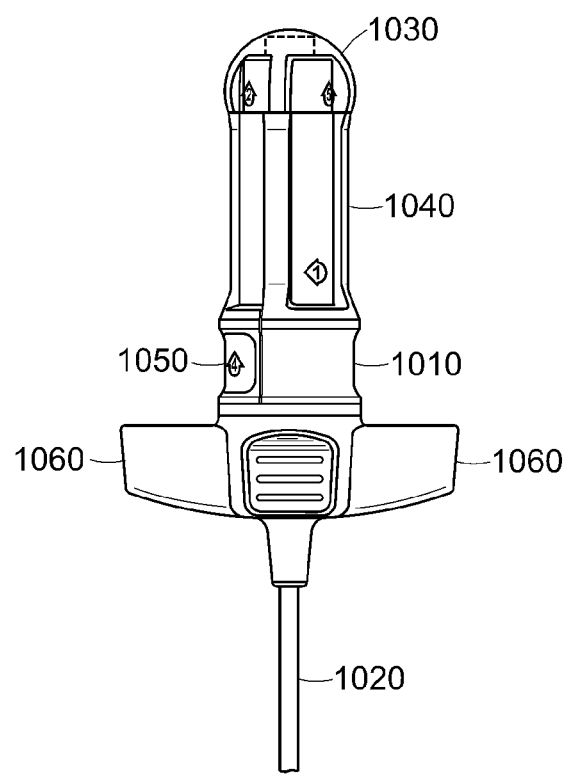
FIG. 10C is a schematic plan view of the handle of FIG. 10A.

Another example delivery system 1000, including a rotating user control mechanism 1040 on the handle 1010, can be seen in FIGS. 10A to 10C. The rotating user control mechanism can include, but is not limited to, a rotational cam mechanism or a rotational threaded mechanism. In an alternative embodiment, a gear mechanism, a sliding belt or triggering mechanism, or any other appropriate mechanism, as described herein, can be used in place of the rotating user control mechanism 1040 to move the inner shaft, outer shaft, and/or sheath, as required.

As with certain other embodiments of the invention described herein, the delivery system 1000 includes a handle 1010, an elongate shaft 1020, including a key component 1025, a top cap 1030, and a number of user interface elements. The user interface elements include a rotating user control mechanism 1040 and two stent release buttons 1050. In an alternative embodiment, a lesser or greater number of stent release buttons can be used. In one embodiment, the stent release buttons 1050 can be replaced by one or more switches, knobs, sliding elements and/or other appropriate user elements, or combinations thereof, as required.

In one embodiment, one or more additional user input mechanisms 1060 can be incorporated into the handle 1010. These user input mechanisms 1060 can include, but are not limited to, delivery system release mechanisms, stent deployment and/or release mechanisms, a mechanism for controlling the curvature of a distal end of one or more of the elongate shafts, or any other appropriate control, delivery, and/or deployment function control elements. In alternative embodiments, the user input mechanisms 1060 can include, but are not limited to, buttons, switches, dials, sliding elements, or other appropriate mechanical or electrical input elements. In one example embodiment, the user input mechanism 1060 is a delivery system release mechanism adapted to allow the delivery system 1000 to be unlocked and disengaged from a cannula or other working channel. Again, any other appropriate user element on the delivery system 1000 and/or cannula can be used to release the delivery system 1000 from the cannula upon completion of the stent deployment. In a further alternative embodiment, there are no additional user input mechanisms 1060.

Figure 11A:
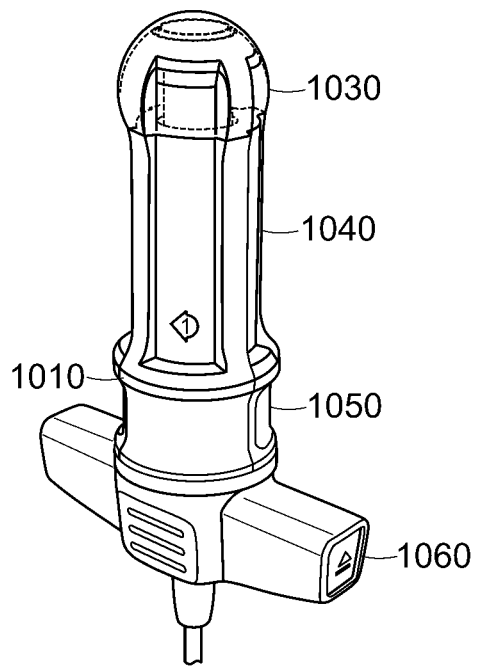
FIG. 11A is a schematic perspective view of the handle of FIG. 10A.
Figure 11B:
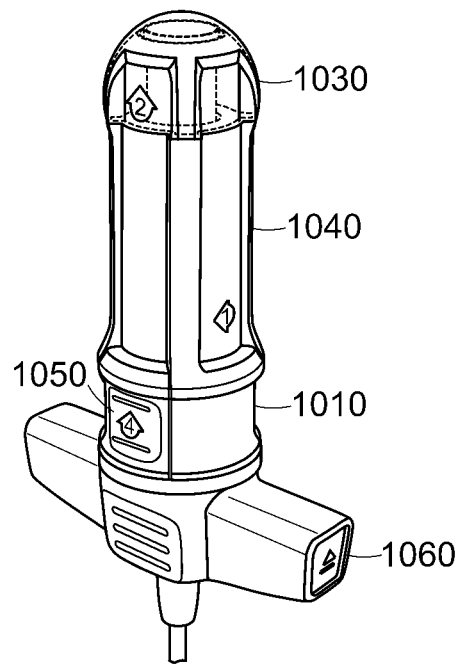
FIG. 11B is a schematic perspective view of the handle of FIG. 11A after rotation of a rotating user control mechanism.

A method of using the delivery system 1000, in accordance with one embodiment of the invention, can be seen in FIGS. 11A to 11D. This embodiment includes first inserting the delivery system 1000 into the cannula and locking it in position in a predetermined set orientation. FIG. 11A shows the delivery system 1000 in its initial configuration after insertion into a cannula (not shown). The rotating user control mechanism 1040 on the handle 1010 of the delivery system 1000 can then be rotated, resulting in the outer sheath of the elongate shaft being retracted while the inner and outer shafts are moved forward to compensate for any foreshortening of the stent during retraction of the sheath, as described above. FIG. 11 B shows the delivery systems 1000 after rotation of the rotating user control mechanism 1040.

Figure 11C:
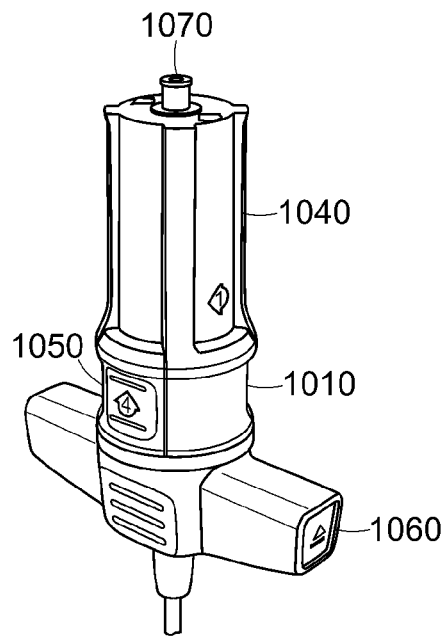
FIG. 11C is a schematic perspective view of the handle of FIG. 11B after removal of the top cap.

Once the sheath has been retracted, the top cap 1030 of the handle 1010 can be removed, and a syringe or other cement deployment device can be attached to a luer lock 1070 (or other appropriate connection means) at the proximal end of the handle 1010. FIG. 11C shows the handle 1010 with a top cap 1030 removed. Cement can then be injected through the delivery system 1000 and into the stent. Once the required amount of cement has been delivered into the stent, the syringe can be removed.

Figure 11D:
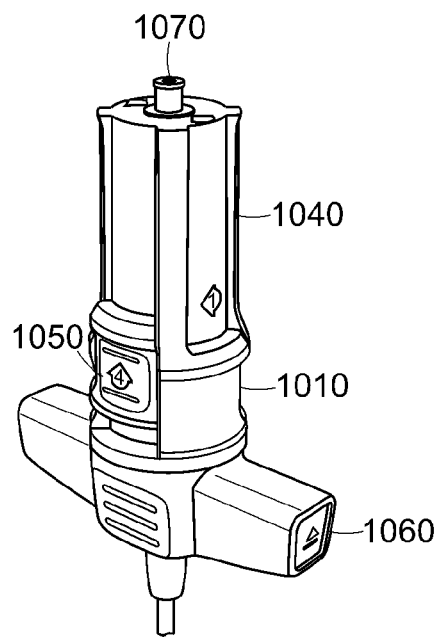
FIG. 11D is a schematic perspective view of the handle of FIG. 11C after depression of sliding of the stent release buttons.

The stent release buttons 1050 can then be depressed and slid towards the proximal end of the handle 1010 (i.e. away from the elongate shaft 1020) to release the stent from the elongate shaft 1020. FIG. 11D shows the delivery system 1000 with the stent release buttons 1050 depressed and slid towards the proximal end of the handle 1010 to release the stent. The delivery system 1000 can then be safely removed by activating a delivery system release button, or other appropriate mechanism, to disengage the delivery system 1000 from the locking mechanism on the cannula, and removing the delivery system 1000 from the cannula while leaving the disengaged stent within the vertebral body.

In one embodiment of the invention, a distal end of an elongate shaft can include a preformed curvature. The elongate shaft can include, but is not limited to, an inner shaft, an outer shaft, a tubular sheath, a flexible guidewire, and an internal polymer extrusion. The elongate shaft, or a portion thereof, can be constructed from a metal including, but not limited to, nitinol, steel, aluminum, or any other appropriate material such as, but not limited to, a plastic. The distal end of the elongate shaft can also include a slotted arrangement allowing the distal end of the elongate shaft to curve and/or preferentially buckle in a specified direction. This curving of the distal end of the elongate shaft can be controlled by a curvature control mechanism located, for example, within the handle of the delivery system. In an alternative embodiment, the elongate shaft can preferentially buckle in response to a force imposed on the distal end of the elongate shaft by the surrounding bone and/or tissue within the vertebral body. Example elongate shafts with preformed and controlled curvature and/or preferential buckling are described in the related U.S. patent application Docket No. SOT-004, entitled "Devices and Methods for Vertebrostenting," and filed of even date herewith, and U.S. application Ser. No. 11/091,232, the disclosures of which are being incorporated herein by reference in their entirety.

In one embodiment of the invention, a stent for use with the apparatus and methods described herein can include an attachment mechanism at a distal end thereof (i.e. at the end of the stent remote from the elongate shaft). This attachment mechanism can releasably attach to one or more elongate elements extending through the interior of the elongate shaft.

In operation of one embodiment, the elongate element extending through the elongate shaft and attaching to the distal end of the stent can be used to hold the stent in a collapsed configuration prior to deployment in place of, or in addition to, a sheath. When the stent is ready to be deployed, the attached elongate element can be used to pull the distal end of the stent rearwards towards its proximate end (i.e. the end of the stent releasably attached to the distal end of the elongate shaft) in order to assist in expanding or to forcibly expand the stent. This may be advantageous in embodiments of the invention using a stiffer and/or thicker stent, that may benefit from additional external forces to assist in its expansion or to provide positive forces on the walls of a cavity in which it is inserted. For example, a stiffer stent, with a more substantive mesh structure, can be used to provide a jacking force to expand the size of a cavity and/or jack or push two walls of a collapsed vertebral body apart. In this embodiment, the self-expanding nature of the stent may not provide sufficient force in and of itself to provide a jacking force of desired magnitude. The additional force needed to allow the stent to jack the walls apart can be provided by the pulling force applied to the distal end of the stent by the releasably attached elongate element. After the stent has been expanded, the elongate element can be released from the stent and removed through the elongate shaft.

The elongate element releasably attached to the distal end of the stent can also be advantageous in embodiments where a cavity has not been reamed out in the vertebral body, or other structure, but rather only a drill hole has been created in the vertebral body sufficient in size to receive the stent in a collapsed configuration. In this embodiment, the elongate element can be used to pull on the distal end of the stent and assist in expanding it into the body structure surrounding the drill hole. This method may be useful, for example, in the treatment of seriously degraded vertebral bodies, where the stent can be expanded into the surrounding degraded bony structure with nominal additional force.

An example stent deployment method including a stent with an attachment mechanism at its distal end can be seen in FIGS. 12A to 12D. In this embodiment, a stent 1205 is releasably attached at its proximal end 1210 to an elongate shaft 1215 including an inner shaft 1220 and an outer shaft 1225. The means of releasably attaching the stent 1205 to the elongate shaft can include any of the mechanisms and methods described herein.

A ferrule 1230 is placed against the interior wall of the distal end 1235 of the stent 1205, with a locking ring 1240 holding the ferrule 1230 in place against the wall of the distal end 1235 of the stent 1205, for example by a radial interference fit. The ferrule includes a hollow proximate end 1245 with two slots 1250 formed in the walls thereof. The slots 1250 are adapted to releasably engage an elongate attachment element 1255 with a pair of tangs 1260 at a distal end thereof. The tangs 1260 are bent in towards the central axis 1275 of the elongate attachment element 1255 such that the tips 1265 of the tangs 1260 can be extended into the hollow proximate end 1245 of the ferrule 1230. In an alternative embodiment, a greater or lesser number of slots 1250 and corresponding tangs 1260 can be used.

Once the tips 1265 of the tangs 1260 have been extended into the hollow proximate end 1245 of the ferrule 1230, an inner rod 1270 is extended through the elongate attachment element 1255 to abut against the inner walls of the tangs 1260. By pushing the inner rod 1270 forward towards the distal end 1235 of the stent 1205, the inner rod 1270 pushes the ends of the tangs 1260 outwards from the central axis 1275 of the elongate attachment element 1255 such that the tips 1265 are forced into the slots 1250 in the ferrule 1230. As a result, the elongate attachment element 1255 becomes releasably coupled to the ferrule 1230 and can therefore provide a pulling force to the distal end 1235 of the stent 1205.

In operation, the elongate attachment element 1255 is coupled to the ferrule 1230 prior to deploying the stent 1205 in the vertebral body. To facilitate insertion of the stent 1205 through the cannula, and into the vertebral body, the elongate attachment element 1255 is pushed forwards against the distal end 1235 of the stent 1205 to force the stent 1205 into a collapsed configuration, as shown in FIG. 12A. In one embodiment a sheath can be extended over the stent 1205 to hold the stent 1205 in a collapsed configuration, with the sheath being retracted once the stent 1205 is in position within the vertebral body, as described above. In an alternative embodiment, no sheath is required, with the elongate attachment element 1255 providing sufficient force to maintain the stent 1205 in a collapsed configuration.

Once the stent 1205 has been positioned correctly within the vertebral body, the elongate attachment element 1255 can be pulled back by a set amount, dependent upon the size and shape of the stent 1205, thus pulling on the distal end 1235 of the stent 1205 and forcing it to expand to its deployed configuration, as shown in FIG. 12B. Advantageously, as the distal end 1235 of the stent 1205 is pulled back, the proximal end 1210 of the stent can be advanced or pushed forward, in order to expand the stent 1205 while leaving a midpoint of the stent 1205 in essentially a fixed position in the cavity in the vertebral body. This coordinated action of retracting the distal end 1235 while advancing the proximal end 1210 can be accomplished using the types of mechanisms described above located in the handle.

After the stent 1205 has been positioned in its deployed configuration, the inner rod 1270 can be pulled out from the elongate attachment element 1255, as shown in FIG. 12C. As the inner rod 1270 is pulled out, the tangs 1260 collapse back into their initial configuration (i.e. bent in towards the central axis 1275 of the elongate attachment element 1255). This in turn removes the tips 1265 of the tangs 1260 from the slots 1250 of the ferrule 1230, thus disengaging the elongate attachment element 1255 from the ferrule 1230. The elongate attachment element 1255 can then be pulled out from the ferrule, leaving the distal end 1235 of the stent 1205 free.

In one embodiment, the elongate attachment element 1255 is a hollow needle adapted to inject cement into the stent 1205. In operation, once the inner rod 1270 has been removed and the elongate attachment element 1255 detached from the ferrule 1230, cement can be injected through the elongate attachment element 1255 and into the interior of the stent 1205 to fill the stent 1205, as shown in FIG. 12D. After the stent 1205 has been filled with cement to the volume required, the elongate attachment element 1255 can be removed and the stent 1205 detached from the elongate shaft. In an alternative embodiment, the elongate attachment element 1255 can simply be removed from the elongate shaft 1215 after deployment of the stent 1205, with cement, or any other appropriate filler material, being injected thereafter into the stent 1205 directly through the inner shaft 1220 of the elongate shaft 1215, or through a separate cement injection element.

The elongate attachment element 1255, elongate shaft 1215, ferrule 1230, locking ring 1240, and inner rod 1270 can be constructed from materials including, but not limited to, a metal (e.g. nitinol, steel, aluminum, or any other appropriate metal), a plastic, and/or a composite material.

In an alternative embodiment, the ferrule 1230 can be attached to the distal end 1235 of the stent 1205 by any other appropriate method, such as, but not limited to, being glued to, welded to, or otherwise attached to the stent 1205. In further alternative embodiments, the elongate attachment element 1255 can be releasably attached to the ferrule by any appropriate mechanical, electrical, thermal, or magnetic connection means.

In alternative embodiments of the invention, any appropriate material, or combination of materials, may be used for the components of the delivery system. Appropriate materials include, but are not limited to, stainless steel, aluminum, plastics, textiles (for the sheath), composite materials, or any combination thereof. The delivery system may be configured with all, or only some of, the components described herein, depending upon the specific requirements of the system.

The delivery system may be configured to deliver cement, cement analogue, or other appropriate filler material, to any appropriate stent, bag, or other fillable device. In one embodiment, the stent need not have holes for the directed exit of the cement into the vertebral body. The delivery system may be configured to delivery a stent, or other device, to a cavity in any bony structure, and not just a vertebral body. Additionally, any appropriately shaped cavity may be treated with the above-mentioned delivery system and stents.

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A stent delivery system for deploying a stent within an enlarged curvilinear void created in a bony structure comprising:
   a handle;
   an elongate shaft adapted to releasably hold a self-expanding cement-directing stent at a distal end, wherein the elongate shaft includes an inner shaft, an outer shaft and a tubular sheath; and
   at least one user control mechanism adapted to deploy the stent,
   wherein the at least one user control mechanism includes a rotating user control mechanism and a stent release button, wherein the user control mechanism comprises a slot and a pin associated with each of the inner shaft, outer shaft and tubular sheath, such that rotation of the user control mechanism will force each pin along a direction determined by a respective slot,
   whereing the at least one user control mechanism is positioned in the handle and is used to move the elongate shaft and deploy the stent.

2. The system of claim 1, wherein the at least one user control mechansim comprises a rotating cam mechanism.

3. The system of claim 2, wherein actuating the rotating cam mechansim retracts the sheath towards the handle.

4. The system of claim 3, wherein actuating the rotating cam mechanism simultaneously extends the distal end of at least one of the inner and the outer shaft away from the handle.

5. The system of claim 1, wherein a distal end of the handle comprises an interface element adapted to releasably engage at least a portion of the proximal end of a cannula.

6. The system of claim 1, wherein the stent is flexible and resilient.

7. A user control mechanism for a stent delievery device, comprising:
   a support element, wherein the support element houses an elongate shaft comprising an inner shaft, an outer shaft and a tubular sheath;
   at least one cam shaft helically positioned on the support element; and
   at least one pin engaging the cam shaft corresponding to each of the inner shaft, outer shaft and tubular sheath, wherein the cam shaft is adapted to force the pin linearly along an axial extend of the user control mechanism upon a rotation of the support element,
   whereing the user control mechanism is positioned in the support element and is used to move the elongate shaft and deploy a braided sheath.

* * * * *